(12) United States Patent
Anderson et al.

(10) Patent No.: US 6,648,921 B2
(45) Date of Patent: Nov. 18, 2003

(54) IMPLANTABLE ARTICLE

(75) Inventors: Kimberly A. Anderson, Eagan, MN (US); Johann J. Neisz, Coon Rapids, MN (US); Steven W. Siegel, North Oaks, MN (US)

(73) Assignee: AMS Research Corporation, Minnetonka, MN (US)

( * ) Notice: Subject to any disclaimer, the term of this patent is extended or adjusted under 35 U.S.C. 154(b) by 81 days.

(21) Appl. No.: 10/004,185

(22) Filed: Oct. 30, 2001

(65) Prior Publication Data

US 2003/0065402 A1 Apr. 3, 2003

Related U.S. Application Data

(60) Provisional application No. 60/327,075, filed on Oct. 3, 2001.

(51) Int. Cl.$^7$ .............................. A61B 19/00; A61F 2/00
(52) U.S. Cl. ...................................... 623/23.64; 600/37
(58) Field of Search ........................ 623/23.64–23.66; 600/29, 30, 37

(56) References Cited

U.S. PATENT DOCUMENTS

| | | |
|---|---|---|
| 2,738,790 A | 3/1956 | Todt et al. |
| 3,124,136 A | 3/1964 | Usher |
| 3,182,662 A | 5/1965 | Shirodkar |
| 3,384,073 A | 5/1968 | Van Winkle, Jr. |
| 3,789,828 A | 2/1974 | Schulte |
| 3,995,619 A | 12/1976 | Glatzer |
| 4,019,499 A * | 4/1977 | Fitzgerald .................. 128/898 |
| 4,172,458 A | 10/1979 | Pereyra |
| 4,246,660 A | 1/1981 | Wevers |
| 4,452,245 A | 6/1984 | Usher |
| 4,509,516 A | 4/1985 | Richmond |
| 4,632,100 A | 12/1986 | Somers et al. |
| 4,857,041 A | 8/1989 | Annis et al. |
| 4,920,986 A | 5/1990 | Biswas |
| 4,938,760 A | 7/1990 | Burton et al. |
| 4,969,892 A | 11/1990 | Burton et al. |
| 4,979,956 A | 12/1990 | Silverstrini |
| 5,007,894 A | 4/1991 | Enhorning |
| 5,012,822 A | 5/1991 | Schwarz |
| 5,013,292 A | 5/1991 | Lemay |

(List continued on next page.)

FOREIGN PATENT DOCUMENTS

| | | |
|---|---|---|
| DE | 2305815 | 2/1973 |
| DE | 4220283 C2 | 5/1994 |
| EP | 0 470 308 A1 | 2/1992 |
| EP | 0650703 A1 | 6/1994 |
| EP | 0643945 A2 | 7/1994 |

(List continued on next page.)

OTHER PUBLICATIONS

Araki et al., The Loop–Loosening Procedure for Urination Difficulties after Stamey Suspension of the Vesical Neck, The Journal of Urology, vol. 144, p. 319–323 (Aug. 1990).
Blavis et al., Type III Stress Urinary Incontinence: Importance of Proper Diagnosis and Treatment, Surgical Forum Gynecology and Obstetrics, p. 473–475, (admitted prior art).
Blavis, Jerry G., Commentary: Pubovaginal Sling Procedure, Experience with Pubovaginal Slings, pp. 93–101 (admitted prior art).

(List continued on next page.)

*Primary Examiner*—David H. Willse
*Assistant Examiner*—Suzette J. Jackson
(74) *Attorney, Agent, or Firm*—Jeffrey J. Hohenshell

(57) ABSTRACT

An implantable article is disclosed. The implantable article includes features for tightening or loosening the implantable article. In preferred embodiments, the adjustment may occur post or perioperatively.

31 Claims, 12 Drawing Sheets

U.S. PATENT DOCUMENTS

| | | | |
|---|---|---|---|
| 5,019,032 A | 5/1991 | Robertson | |
| 5,032,508 A | 7/1991 | Naughton et al. | |
| 5,036,867 A | 8/1991 | Biswas | |
| 5,053,043 A | 10/1991 | Gottesman et al. | |
| 5,085,661 A | 2/1992 | Moss | |
| 5,112,344 A | 5/1992 | Petros | |
| 5,123,428 A | 6/1992 | Schwarz | |
| 5,188,636 A | 2/1993 | Fedotov | |
| 5,256,133 A | 10/1993 | Spitz | |
| 5,281,237 A | 1/1994 | Gimpelson | |
| 5,328,077 A | 7/1994 | Lou | |
| 5,337,736 A | 8/1994 | Reddy | |
| 5,362,294 A | 11/1994 | Seitzinger | |
| 5,383,904 A | 1/1995 | Totakura et al. | |
| 5,386,836 A | 2/1995 | Biswas | |
| 5,413,598 A | 5/1995 | Moreland | |
| 5,439,467 A | 8/1995 | Benderev et al. | |
| 5,520,700 A | 5/1996 | Beyar et al. | |
| 5,544,664 A | 8/1996 | Benderev et al. | |
| 5,562,689 A | 10/1996 | Green et al. | |
| 5,571,139 A | 11/1996 | Jenkins, Jr. | |
| 5,591,163 A | 1/1997 | Thompson | |
| 5,611,515 A | 3/1997 | Benderev et al. | |
| 5,633,286 A | 5/1997 | Chen | |
| 5,669,935 A | 9/1997 | Rosenman et al. | |
| 5,683,349 A | 11/1997 | Makower et al. | |
| 5,807,403 A | 9/1998 | Beyar et al. | |
| 5,836,314 A | 11/1998 | Benderev et al. | |
| 5,836,315 A | 11/1998 | Benderev et al. | |
| 5,842,478 A | 12/1998 | Benderev et al. | |
| 5,860,425 A | 1/1999 | Benderev et al. | |
| 5,899,909 A | 5/1999 | Claren et al. | |
| 5,919,232 A * | 7/1999 | Chaffringeon et al. | 600/37 |
| 5,934,283 A | 8/1999 | Willem et al. | |
| 5,944,732 A | 8/1999 | Raulerson et al. | |
| 5,972,000 A | 10/1999 | Beyar et al. | |
| 5,988,171 A | 11/1999 | Sohn et al. | |
| 5,997,554 A | 12/1999 | Thompson | |
| 6,010,447 A * | 1/2000 | Kardjian | 600/29 |
| 6,030,393 A | 2/2000 | Corlew | |
| 6,031,148 A * | 2/2000 | Hayes et al. | 623/11.11 |
| 6,039,686 A | 3/2000 | Kovac | |
| 6,042,534 A * | 3/2000 | Gellman et al. | 623/11.11 |
| 6,042,536 A | 3/2000 | Tihon et al. | |
| 6,050,937 A | 4/2000 | Benderev | |
| 6,068,591 A | 5/2000 | Bruckner et al. | |
| 6,071,290 A | 6/2000 | Compton | |
| 6,106,545 A | 8/2000 | Egan | |
| 6,110,101 A * | 8/2000 | Tihon et al. | 600/37 |
| 6,117,067 A | 9/2000 | Gil-Vernet | |
| 6,168,611 B1 | 1/2001 | Rizvi | |
| 6,221,005 B1 * | 4/2001 | Bruckner et al. | 600/30 |
| 6,273,852 B1 | 8/2001 | Lehe et al. | |
| 6,302,840 B1 | 10/2001 | Benderev | |
| 6,306,079 B1 * | 10/2001 | Trabucco | 600/30 |
| 6,322,492 B1 | 11/2001 | Kovac | |
| 6,328,686 B1 | 12/2001 | Kovac | |
| 6,328,744 B1 | 12/2001 | Harari et al. | |
| 6,334,446 B1 | 1/2002 | Beyar | |
| 6,352,553 B1 * | 3/2002 | van der Burg et al. | 623/1.23 |
| 6,382,214 B1 | 5/2002 | Raz et al. | |
| 6,406,423 B1 | 6/2002 | Scetbon | |
| 6,406,480 B1 | 6/2002 | Beyar et al. | |
| 6,423,080 B1 | 7/2002 | Gellman et al. | |
| 6,475,139 B1 * | 11/2002 | Miller | 600/135 |
| 6,478,727 B2 | 11/2002 | Scetbon | |
| 6,482,214 B1 * | 11/2002 | Sidor, Jr. et al. | 606/151 |
| 6,494,906 B1 * | 12/2002 | Owens | 606/8 |
| 6,502,578 B2 * | 1/2003 | Raz et al. | 128/898 |
| 2001/0018549 A1 | 8/2001 | Scetbon | |
| 2002/0055748 A1 | 5/2002 | Gellman et al. | |
| 2002/0058959 A1 | 5/2002 | Gellman | |
| 2002/0068948 A1 | 6/2002 | Stormby et al. | |
| 2002/0077526 A1 | 6/2002 | Kammerer et al. | |
| 2002/0082619 A1 | 6/2002 | Cabak et al. | |
| 2002/0091373 A1 | 7/2002 | Berger | |
| 2002/0099260 A1 | 7/2002 | Suslian et al. | |
| 2002/0107430 A1 | 8/2002 | Neisz et al. | |
| 2002/0107525 A1 | 8/2002 | Harari et al. | |
| 2002/0115906 A1 | 8/2002 | Miller | |
| 2002/0128670 A1 | 9/2002 | Ulmsten et al. | |
| 2002/0151909 A1 | 10/2002 | Gellman et al. | |
| 2002/0151910 A1 | 10/2002 | Gellman et al. | |
| 2002/0156487 A1 | 10/2002 | Gelllman et al. | |
| 2002/0156488 A1 | 10/2002 | Gellman et al. | |
| 2002/0156489 A1 | 10/2002 | Gellman et al. | |
| 2003/0036676 A1 | 2/2003 | Scetbon | |

FOREIGN PATENT DOCUMENTS

| | | | |
|---|---|---|---|
| EP | 1 093 758 A1 | 4/2001 | |
| SU | 1225547 A1 | 4/1986 | |
| SU | 1342486 A | 10/1987 | |
| WO | WO 93/17635 A1 | 9/1993 | |
| WO | 93/19678 | 10/1993 | |
| WO | WO 98/19606 A1 | 5/1998 | |
| WO | WO 98/35632 A1 | 8/1998 | |
| WO | WO 98/356161 A1 | 8/1998 | |
| WO | 99/52450 | 10/1999 | |
| WO | WO 99/52450 * | 10/1999 | A61B/17/04 |
| WO | 00/13601 | 3/2000 | |
| WO | WO 00/18319 A1 | 4/2000 | |
| WO | WO 00/57812 A1 | 10/2000 | |
| WO | WO 00/64370 A1 | 11/2000 | |
| WO | WO 00/74594 A1 | 12/2000 | |
| WO | WO 00/74613 A1 | 12/2000 | |
| WO | WO 00/74633 A2 | 12/2000 | |
| WO | WO 01/26581 A1 | 4/2001 | |
| WO | 01/39670 A1 | 6/2001 | |
| WO | WO 01/45589 A1 | 6/2001 | |
| WO | 01/56499 A1 | 8/2001 | |
| WO | WO 02/28312 A1 | 4/2002 | |
| WO | WO 02/32284 A2 | 4/2002 | |
| WO | WO 02/34124 A2 | 5/2002 | |

OTHER PUBLICATIONS

Decter, Ross M., Use of the Fascial Sling for Neurogenic Incontinence: Lessons Learned, The Journal of Urology, vol. 150, p. 683–686 (Aug. 1993).

Jeffcoate, T.N.A., The Results of the Aldridge Sling Operation for Stress Incontinence, Journal of Obstetrics and Gynaecology, p. 36–39, 1956.

Kersey, J., The Gauze Hammock Sling Operation in the Treatment of Stress Incontinence, British Journal of Obstetrics and Gynaecology, vol. 90, p. 945–949 (Oct. 1983).

McGuire, Edward J. et al., Abdominal Fascial Slings, Slings, Raz Female Urology, p. 369–375 (1996).

McGuire, Edward J. et al., Experience with Pubovaginal Slings for Urinary Incontinence at the University of Michigan, Journal of Urology, vol. 138, pp. 525–526 (1987).

McIndoe G.A.J. et al., The Aldridge Sling Procedure in the Treatment of Urinary Stress Incontinence, Aust. NZ J Obstet Gynaecol, p. 238–239 (1987).

Moir, J. Chassar, The Gauze–Hammock Operation, The Journal of Obstetrics and Gynaecology of the British Commonwealth, pp. 1–9, vol. 75, No. 1, (Jan. 1968).

Morgan, J.E., A Sling Operation, Using Marlex Polypropylene Mesh for Treatment of Recurrent Stress Incontinence, American Journal of Obst. & Gynec., vol. 106 No. 3, p. 369–377, (Feb. 15, 1970).

Narik. G et al., A Simplified Sling Operation Suitable for Routine Use, American Journal Obstetrics & Gynecology, pp. 400–405, vol. 84 No. 3, (Aug. 1, 1962).

Rackley et al., Tension–Free Vaginal Tape and Percutaneous Vaginal Tape Sling Procedures, Techniques in Urology, vol. 7, No. 2, p. 90–100 (2001).

Ridley, John H., Appraisal of the Goebell–Frangenheim–Stoeckel Sling Procedure, American Journal Obst & Gynec., vol. 95 No. 5, p. 714–721 (Jul. 1, 1966).

Sloan, W.R. et al., Stress Incontinence of Urine: A Retrospective Study of the Complications and Late Results of Simple Suprapubic Suburethral Fascial Slings, Journal of Urology, pp. 533–536, vol. 110, (Nov. 1973).

Spencer et al., A Comparison of Endoscopic Suspension of the Vesical Neck with Suprapubic Vesicourethropexy for Treatment of Stress Urinary Incontinence, The Journal of Urology, vol. 137, p. 411–415 (Mar. 1987).

Stanton, Stuart L., Suprapubic Approaches for Stress Incontinence in Women, Journal of American Geriatrics Society, vol. 38, No. 3, p. 348–351 (Mar. 1990).

Studdiford, William, Transplantation of Abdominal Fascia for the Relief of Urinary Stress Incontinence, American Journal of Obstetrics and Gynecology, pp. 764–775 (no date).

Vesica Sling Kits, Simplifying Sling Procedures, Boston Scientific Microvasive, 4 pages (1998).

Vesica Sling Kits, A New Approach to Bladder Neck Suspension, Boston Scientific Microvasive, 4 pages (1995).

Webster et al., Voiding Dysfunction Following Cystourethropexy: Its Evaluation and Management, The Journal of Urology, vol. 144, p. 670–673 (Sep. 1990).

Asmussen, M. et al., Simultaneous Urethro–Cystometry with a New Technique, Scand J Urol Nephrol 10, p. 7–11 (1976).

Beck, Peter R. et al., Treatment of Urinary Stress Incontinence with Anterior Colporrhaphy, Obstetrics and Gynecology, vol. 59 (No. 3), pp. 269–274 (Mar. 1982).

Benderev, Theodore V., MD, A Modified Percutaneous Outpatient Bladder Neck Suspension System, Journal of Urology, vol. 152, pp. 2316–2320 (Dec. 1994).

Benderev, Theodore V., MD, Anchor Fixation and Other Modifications of Endoscopic Bladder Neck Suspension, Urology, vol. 40, No. 5, pp. 409–418 (Nov. 1992).

Bergman, Arieh et al., Three Surgical Procedures for Genuine Stress Incontinence: Five–Year Follow–Up of a Prospective Randomized Study, Am J Obstet Gynecol, vol. 173 No. 1, pp. 66–71 (Jul. 1995).

Blaivas, Jerry et al., Pubovaginal Fascial Sling for the Treatment of Complicated Stress Urinary Incontinence, The Journal of Urology, vol. 145, pp. 1214–1218 (Jun. 1991).

Blavis, Jerry, Commentary: Pubovaginal Sling Procedure, Experience with Pubovaginal Slings, pp. 93–101.

Bryans, Fred E., Marlex Gauze Hammock Sling Operation with Cooper's Ligament Attachment in the Management of Recurrent Urinary Stress Incontinence, American Journal of Obstetrics and Gynecology, vol. 133, pp. 292–294 (Feb. 1979).

Burch, John C., Urethrovaginal Fixation to Cooper's Ligament for Correction of Stress Incontinence, Cystocele, and Prolapse, Am. J. Obst. & Gyn, vol. 31, pp. 281–290 (1961).

Choe, Jong M. et al., Gore–Tex Patch Sling: 7 Years Later, Urology, vol. 54, pp. 641–646 (1999).

Cook/Ob Gyn®, Urogynecology, Copyright Cook Urological Inc., pp. 1–36 (1996).

Das, Sakti et al., Laparoscopic Colpo–Suspension, The Journal of Urology, vol. 154, pp. 1119–1121 (Sep. 1995).

DeLancey, John, MD, Structural Support of the Urethra as it Relates to Stress Urinary Incontinence: The Hammock Hypothesis, Am J Obstet Gynecol, vol. 170 No. 6, pp. 1713–1723 (Jun. 1994).

Enzelsberger, H. et al., Urodynamic and Radiologic Parameters Before and After Loop Surgery for Recurrent Urinary Stress Incontinence, Acta Obstet Gynecol Scand, 69, pp. 51–54 (1990).

Eriksen, Bjarne C. et al., Long–Term Effectiveness of the Burch Colposuspension in Female Urinary Stress Incontinence, Acta Obstet Gynecol Scand, 69, pp. 45–50 (1990).

Falconer, C. et al., Clinical Outcome and Changes in Connective Tissue Metabolism After Intravaginal Slingplasty in Stress Incontinence Women, International Urogynecology Journal, pp. 133–137 (1966).

Falconer, C. et al., Influence of Different Sling Materials of Connective Tissue Metabolism in Stress Urinary Incontinent Women, International Urogynecology Journal, Supp. 2, pp. S19–S23 (2001).

Gilja, Ivan et al., A Modified Raz Bladder Neck Suspension Operation (Transvaginal Burch), The Journal of Urology, vol. 153, pp. 1455–1457 (May 1995).

Gittes, Ruben F. et al., No–Incision Pubovaginal Suspension for Stress Incontinence, The Journal of Urology, vol. 138 (Sep. 1987).

Handa, Victoria L. et al., Banked Human Fascia Lata for the Suburethral Sling Procedure: A Preliminary Report, Obstetrics & Gynecology, vol. 88 No. 6, 5 pages (Dec. 1996).

Henriksson, L. et al., A Urodynamic Evaluation of the Effects of Abdominal Urethrocystopexy and Vaginal Sling Urethroplasty in Women with Stress Incontinence, Am. J. Obstet. Gynecol. vol. 131, No. 1, pp. 77–82 (Mar. 1, 1978).

Hodgkinson, C. Paul et al., Urinary Stress Incontinence in the Female, Department of Gynecology and Obstetrics, Henry Ford Hospital, vol. 10, No. 5, p. 493–499, (Nov. 1957).

Holschneider, C. H., et al., The Modified Pereyra Procedure in Recurrent Stress Urinary Incontinence: A 15–year Review, Obstetrics & Gynecology, vol. 83, No. 4, pp. 573–578 (Apr. 1994).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648–652 (Apr. 1998).

Ingelman–Sunberg, A. et al., Surgical Treatment of Female Urinary Stress Incontinence, Contr. Gynec. Obstet., vol. 10, pp. 51–69 (1983).

IVS Tunneller, AMA, (no date) 4 pages.

Karram, Mickey et al., Patch Procedure: Modified Transvaginal Fascia Lata Sling for Recurrent for Severe Stress Urinary Incontinence, vol. 75, pp. 461–463 (Mar. 1990).

Klutke, Carl et al., The Anatomy of Stress Incontinence: Magnetic Resonance Imaging of the Female Bladder Neck and Urethra, The Journal of Urology, vol. 143, pp. 563–566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294–296 (Aug. 1996).

Klutke, John M.D. et al, The promise of tension–free vaginal tape for female SUI, Contemporary Urology, 7 pages (Oct. 2000).

Korda, A. et al., Experience with Silastic Slings for Female Urinary Incontience, Aust NZ J. Obstet Gynaecol, vol. 29, pp. 150–154 (May 1989).

Kovac, S. Robert, et al, Pubic Bone Suburethral Stabilization Sling for Recurrent Urinary Incontinence, Obstetrics & Gynecology, vol. 89, No. 4, pp. 624–627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow–up of the Pubic Bone Suburethral Stabilization Sling Operation for Recurrent Urinary Incontinence (Kovac Procedure), Journal of Pelvic Surgery, pp. 156–160 (May 1999).

Leach, Gary E., et al., Female Stress Urinary Incontinence Clinical Guidelines Panel Report on Surgical Management of Female Stress Urinary Incontinence, American Urological Association, vol. 158, pp. 875–880 (Sep. 1997).

Leach, Gary E., MD, Bone Fixation Technique for Transvaginal Needle Suspension, Urology vol. XXXI, No. 5, pp. 388–390 (May 1988).

Lichtenstein, Irving L. et al., The Tension Free Hernioplasty, The American Journal of Surgery, vol. 157 pp. 188–193 (Feb. 1989).

Loughlin, Kevin R. et al., Review of an 8–Year Experience with Modifications of Endoscopic Suspension of the Bladder Neck for Female Stress Incontinence, The Journal of Uroloyg, vol. 143, pp. 44–45 (1990).

Marshall, Victor Fray et al., The Correction of Stress Incontinence by Simple Vesicourethral Suspension, Surgery, Gynecology and Obstetrics, vol. 88, pp. 509–518 (1949).

McGuire, Edward J. et al., Pubovaginal Sling Procedure for Stress Incontinence, The Journal of Urology, vol. 119, pp. 82–84 (Jan. 1978).

McGuire, Edward J. et al., Abdominal Procedures for Stress Incontinence, Urologic Clinics of North America, pp. 285–290, vol. 12, No. 2 (May 1985).

McGuire, Edwared J., M.D., The Sling Procedure for Urinary Stress Incontinence, Profiles in Urology, pp. 3–18.

McKiel, Charles F. Jr., et al, Marshall–Marchetti Procedure Modification, vol. 96, pp. 737–739 (Nov. 1966).

Mitek Brochure, Therapy of Urinary Stess Incontinence in Women Using Mitek GIII Anchors, by Valenzio C. Mascio, MD.

Morgan, J. E. et al., The Marlex Sling Operation for the Treatment of Recurrent Stress Urinary Incontinence: A 16–Year Review, American Obstetrics Gynecology, vol. 151, No. 2, pp. 224–226 (Jan. 1998).

Nichols, David H., The Mersilene Mesh Gauze–Hammock for Severe Urinary Stress Incontinence, Obstetrics and Gynecology, vol. 41, pp. 88–93 (Jan. 1973).

Norris, Jeffrey P., et al., Use of Synthetic Material in Sling Surgery: A Minimally Invasive Approach, Journal of Endourology, vol. 10, pp. 227–230 (Jun. 1996).

O'Donnell, Pat, Combined RAZ Urethral Suspension and McGuire Pubovaginal Sling for Treatment of Complicated Stress Urinary Incontinence, Journal Arkansas Medical Society, vol. 88, pp. 389–392 (Jan. 1992).

Ostergard, Donald R. et al., Urogynecology and Urodynamics Theory and Practice, pp. 569–579 (1996).

Parra, R. O., et al, Experience with a Simplified Technique for the Treatment of Female Stress Urinary Incontinence, British Journal of Urology, pp. 615–617 (1990).

Pelosi, Marco Antonio, III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45–50 (1999).

Pereyra, Armand J. et al, Pubourethral Supports in Perspective: Modified Pereyra Procedure for Urinary Incontinence, Obstetrics and Gynecology, vol. 59, No. 5, pp. 643–648 (May 1982).

Pereyra, Armand J., M.D., F.A.C.S., A Simplified Surgical Procedure for Correction of Stress Incontinence in Women, West.J.Surg., Obst. & Gynec, p. 223–226, (Jul.–Aug. 1959).

Peter E. Papa Petros et al., Cure of Stress Incontinence by Repair of External Anal Sphincter, Acta Obstet Gynecol Scand, vol. 69, Sup 153, p. 75 (1990).

Peter Petros et al., Anchoring the Midurethra Restores Bladder–Neck Anatomy and Continence, The Lancet, vol. 354, pp. 997–998 (Sep. 18, 1999).

Petros, Peter E. Papa et al., An Anatomical Basis for Success and Failure of Female Incontinence Surgery, Scandinavian Journal of Neurourology and Urodynamics, Sup 153, pp. 55–60 (1993).

Petros, Peter E. Papa et al., An Analysis of Rapid Pad Testing and the History for the Diagnosis of Stress Incontinence, Acta Obstet Gynecol Scand, vol. 71, pp. 529–536 (1992).

Petros, Peter E. Papa et al., An Integral Therory of Female Urinary Incontinence, Acta Obstetricia et Gynecologica Scandinavica, vol. 69 Sup. 153, pp. 7–31 (1990).

Petros, Peter E. Papa et al., Bladder Instability in Women: A Premature Activation of the Micturition Reflex, Scandinavian Journal of Neurourology and Urodynamics, Sup 153, pp. 235–239 (1993).

Petros, Peter E. Papa et al., Cough Transmission Ratio: An Indicator of Suburethral Vaginal Wall Tension Rather than Urethral Closure?, Acta Obstet Gynecol Scand, vol. 69, Sup 153, pp. 37–39 (1990).

Petros, Peter E. Papa et al., Cure of Urge Incontinence by the Combined Intravaginal Sling and Tuck Operation, Acta Obstet Gynecol Scand, vol. 69, Sup 153, pp. 61–62 (1990).

Petros, Peter E. Papa et al., Further Development of the Intravaginal Slingplasty Procedure—IVS III—(with Midline "Tuck"), Scandinavian Journal of Neurourology and Urodynamics, Sup 153, p. 69–71 (1993).

Petros, Peter E. Papa et al., Medium–Term Follow–up of the Intravaginal Slingplasty Operation Indicates Minimal Deterioration of Urinary Continence with Time, (3 pages) (1999).

Petros, Peter E. Papa et al., Non Stress Non Urge Female Urinary Incontinence—Diagnosis and Cure:A Preliminary Report, Acta Obstet Gynecol Scand, vol. 69, Sup 153, pp. 69–70 (1990).

Petros, Peter E. Papa et al., Part I: Theoretical, Morphological, Radiographical Correlations and Clinical Perspective, Scandinavian Journal of Neurourology and Urodynamics, Sup 153, pp. 5–28 (1993).

Petros, Peter E. Papa et al., Part II: The Biomechanics of Vaginal Tissue and Supporting Ligaments with Special Relevance to the Pathogenesis of Female Urinary Incontinence, Scandinavian Journal of Neurourology and Urodynamics, Sup 153, pp. 29–40 plus cover sheet (1993).

Petros, Peter E. Papa et al., Part III: Surgical Principles Deriving from the Theory, Scandinavian Journal of Neurourology and Urodynamics, Sup 153, pp. 41–52 (1993).

Petros, Peter E. Papa et al., Part IV: Surgical Appliations of the Theory—Development of the Intravaginal Sling Pklasty (IVS) Procedure, Scandinavian Journal of Neurourology and Urodynamics, Sup 153, pp. 53–54 (1993).

Petros, Peter E. Papa, Development of Generic Models for Ambulatory Vaginal Surgery—Preliminary Report, International Urogynecology Journal, pp. 20–27 (1998).

Petros, Peter E. Papa et al., Pelvic Floor Rehabilitation According to the Integrated Theory of Female Urinary Incontinence, Chapter 7, pp. 249–258 (book chapter).

Petros, Peter E. Papa et al., Pinch Test for Diagnosis of Stress Urinary Incontinence, Acta Obstet Gynecol Scand, vol. 69, Sup 153, pp. 33–35 (1990).

Petros, Peter E. Papa et al., Pregnancy Effects on the Intravaginal Sling Operation, Acta Obstet Gynecol Scand, vol. 69, Sup 153, pp. 77–79 (1990).

Petros, Peter E. Papa et al., The Autogenic Ligament Procedure: A Technique for Planned Formation of an Artificial Neo–Ligament, Acta Obstet Gynecol Scand, vol. 69, Sup 153, pp. 43–51 (1990).

Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53–59 (1990).

Petros, Peter E. Papa et al., The Development of the Intravaginal Slingplasty Procedure: IVSII—(with Bilateral "Tucks"), Scandinavian Journal of Neurourology and Urodynamics, Sup 153, pp. 61–67 (1993).

Petros, Peter E. Papa et al., The Free Graft Procedure for Cure of the Tethered Vagina Syndrome, Scandinavian Journal of Neurourology and Urodynamics, Sup 153, pp. 85–87 (1993).

Petros, Peter E. Papa et al., The Further Development of the Intravaginal Slingplasty Procedure—IVS IV—(with "Double Breasted" Unattached Vaginal Flap Repair and "Free" Vaginal Tapes), Scandanavian Journal of Neurourology and Urodynamics, Sup 153, p. 73–75 (1993).

Petros, Peter E. Papa et al., The Further Development of the Intravaginal Slingplasty Procedure—IVS V—(with "Double Breasted" Unattached Vaginal Flap Repair and Permanent Sling)., Scandinavian Journal of Neurourology and Urodynamics, Sup 153, pp. 77–79 (1993).

Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81–84 (1993).

Petros, Peter E. Papa et al., The Posterior Fornix Syndrome: A Multiple Symptom Complex of Pelvic Pain and Abnormal Urinary Symptoms Deriving from Laxity in the Posterior Fornix of Vagina, Scandinavian Journal of Neurourology and Urodynamics, Sup 153, pp. 89–93 (1993).

Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71–73 (1990).

Petros, Peter E. Papa et al., The Tethered Vagina Syndrome, Post Surgical Incontinence and I–Plasty Operation for Cure, Acta Obstet Gynecol Scand, vol. 69, Sup 153, pp. 63–67 (1990).

Petros, Peter E. Papa et al., The Tuck Procedure: A Simplified Vaginal Repair for Treatment of Female Urinary Incontinence, Acta Obstet Gynecol Scand, vol. 69, Sup 153, pp. 41–42 (1990).

Petros, Peter E. Papa et al., Urethral Pressure Increase on Effort Originates from Within the Urethra, and Continence from Musculovaginal Closure, Scandinavian Journal of Neurourology and Urodynamics, pp. 337–350 (1995).

Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270–278, (1997).

Rackley, Raymond R. M.D., Synthetic Slings: Five Steps for Successful Placement, Urology Times, p. 46,48,49 (Jun. 2000).

Raz, Shlomo, et al., The Raz Bladder Neck Suspension Results in 206 Patients, The Journal of Urology, pp. 845–846 (1992).

Raz, Shlomo, Female Urology, pp. 80–86, 369–398, 435–442 (1996).

Raz, Shlomo, MD, Modified Bladder Neck Suspension for Female Stress Incontinence, Urology, vol. XVII, No. 1, pp. 82–85 (Jan. 1981).

Richardson, David A. et al., Delayed Reaction to the Dacron Buttress Used in Urethropexy, The Journal of Reproductive Medicine, pp. 689–692, vol. 29, No. 9 (Sep. 1984).

Roberts, Henry, M.D., Cystourethrography in Women, Deptment of Obstetrics and Gynaecology, University of Liverpool, May 1952, vol. XXXV, No. 293, pp. 253–259.

Stamey, Thomas A., M.D., Endoscopic Suspension of the Vesical Neck for Urinary Incontinence in Females, Ann. Surgery, vol. 192 No. 4, pp. 465–471 (Oct. 1980).

Stanton, Stuart, Springer–Veglag, Surgery of Female Incontinence, pp. 105–113 (1986).

Staskin et al., A Comparison of Tensile Strength Among Three Preparations of Irradiated and Non–Irradiated Human Fascia Lata Allografts, 2 pages (1992).

Staskin, David R. et al., The Gore–Tex Sling Procedure for Female Sphincteric Incontinence: Indications, Technique, and Results, World Journal of Urology, vol. 15, pp. 295–299 (1997).

Studdiford, William E., Transplantation of Abdominal Fascia for the Relief of Urinary Stress Incontinence, American Journal of Obstetrics and Gynecology, pp. 764–775 (1944).

Suport™, Sub–Urethral Perineal Retro–Pubic Tensionless Sling, Matrix Medical (Pty) Ltd, (no date), 1 pg.

TVT Tension–free Vaginal Tape, Gynecare, Ethicon, Inc., 23 pages (1999).

Ulmsten, U. et al., A Multicenter Study of Tension–Free Vaginal Tape (TVT) for Surgical Treatment of Stress Urinary Incontinence, International Urogynecology Journal, vol. 9, pp. 210–213 (1998).

Ulmsten, U. et al., An Ambulatory Surgical Procedure Under Local Anesthesia for Treatment of Female Urinary Incontinence, International Urogynecology Journal, vol. 7, pp. 81–86 (May 1996).

Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2–3 (1995).

Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345–350 (1999).

Ulmsten, Ulf et al., Different Biochemical Composition of Connective Tissue In–Continent, Acta Obstet Gynecol Scand, pp. 455–457 (1987).

Ulmsten, Ulf et al., Intravaginal Slingplasty (IVS): An Ambulatory Surgical Procedure for Treatment of Female Urinary Incontinence, Scand J Urol Nephrol, vol. 29, pp. 75–82 (1995).

Ulmsten, Ulf et al., The Unstable Female Urethra, Am. J. Obstet. Gynecol., vol. 144 No. 1, pp. 93–97 (Sep. 1, 1982).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93–100, vol. 21 (Mar. 1996).

Webster, George D., Female Urinary Incontinence, Urologic Surgery, pp. 665–679.

Winter, Chester C., Peripubic Urethropexy for Urinary Stress Incontinence in Women, Urology, vol. XX, No. 4, pp. 408–411 (Oct. 1982).

Woodside, Jeffrey R. et al., Suprapubic Endoscopic Vesical Neck Suspension for the Management of Urinary Incontinence in Myelodysplastic Girls, The Journal of Urology, vol. 135, pp. 97–99 (Jan. 1986).

Zacharin, Robert et al., Pulsion Enterocele: Long–Term Results of an Abdominoperineal Technique, Obstetrics & Gynecology, vol. 55 No. 2, pp. 141–148 (Feb. 1980).

Zacharin, Robert, The Suspensory Mechanism of the Female Urethra, Journal of Anatomy, vol. 97, Part 3, pp. 423–427 (1963).

Zimmern, Phillippe E. et al., Four–Corner Bladder Neck Suspension, Vaginal Surgery for the Urologist, vol. 2, No. 1, pp. 29–36 (Apr. 1994).

* cited by examiner

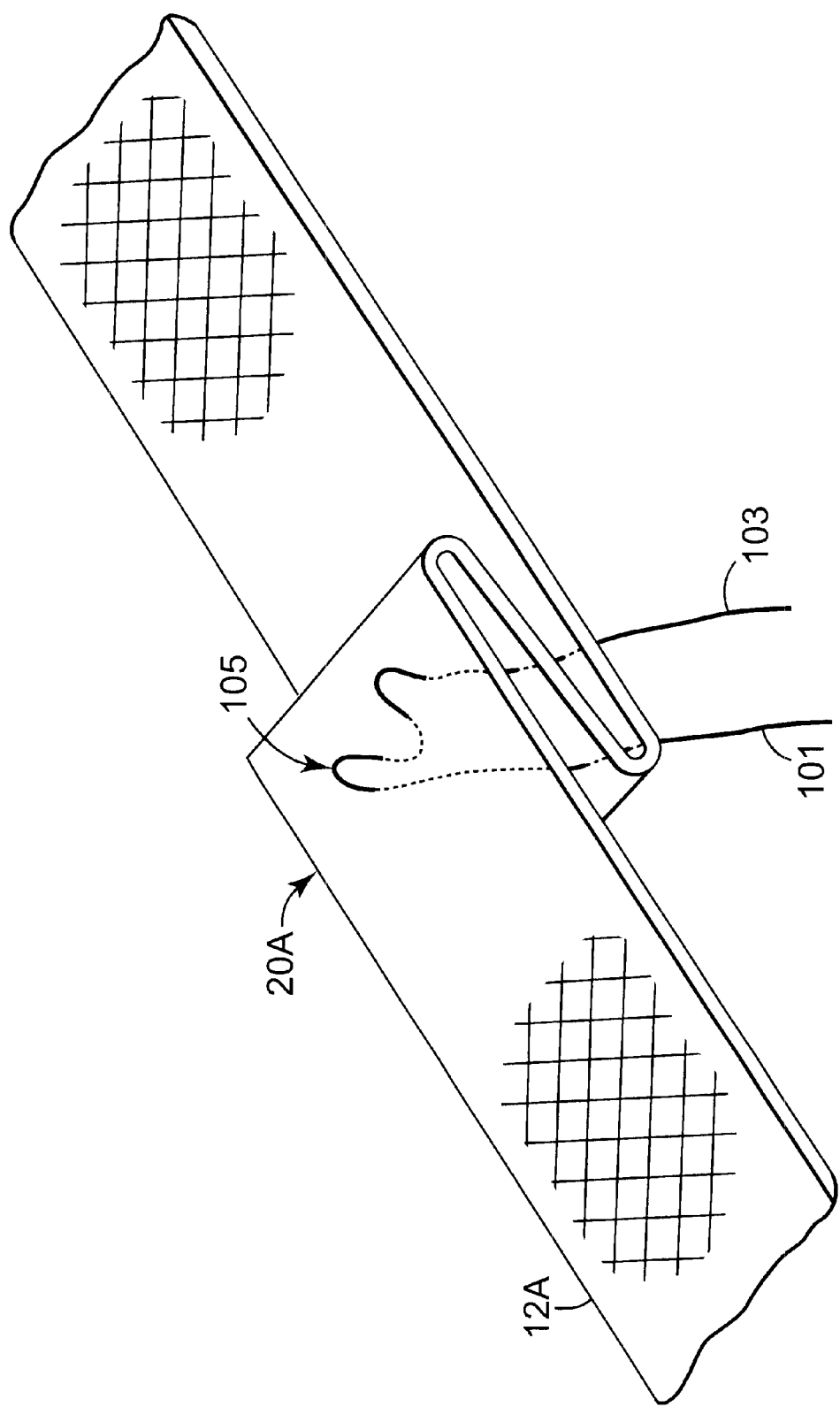

IMPLANTABLE ARTICLE

This application claims priority from U.S. Provisional Patent Application No. 60/327,075, filed Oct. 3, 2001.

BACKGROUND

Urinary incontinence, or the inability to control urination, is a major and debilitating problem affecting millions of people, especially women. The female's natural support system for the urethra is a hammock-like supportive layer composed of endopelvic fascia, the anterior vaginal wall, and a distal attachment to the pubic bone. Weakening and elongation of the pubourethral ligaments and the arcus tendineus fascia pelvis, weakening of the endopelvic fascia, and pubourethral prolapse of the anterior vaginal wall are some common characteristics of a patient with urinary incontinence.

Many procedures have been devised to treat urinary incontinence. Some have the goal of elevating the neck of the bladder to return it to a higher retropubic position. Many pubovaginal sling procedures have been developed to treat urinary incontinence. Some of these procedures involve positioning sling material under the urethra to provide elevation and support of the mid-urethra and/or the bladder neck. Examples of attachment sites for the sling include the anterior or superior portion of the pubis (e.g. with bone anchors and associated sutures), Cooper's ligament, or rectus abdominus fascia. Examples of procedures for treating incontinence are disclosed in U.S. Pat. Nos. 5,112,344; 5,611,515; 5,842,478; 5,860,425; 5,899,909; 6,039,686; 6,042,534 and 6,110,101.

Slings used for pubovaginal procedures differ in the type of implantable material and anchoring methods. In some cases, the sling is placed under the bladder neck and secured via suspension sutures to a point of attachment (e.g. bone) through an abdominal and/or vaginal incision.

Complications associated with procedures for treating incontinence include urinary retention, bladder instability and erosion of an implanted article into surrounding tissue. See Spencer et al, *A Comparison of Endoscopic Suspension of the Vesical Neck With Suprapubic Vesicourethropexy for Treatment of Stress Urinary Incontinence*, J. Urol. 137: 411, (1987); Araki et al, *The Loop Loosening Procedure for Urination Difficulties After Stamey Suspension of the Vesical Neck*, J. Urol., 144; (1990); and Webster et al., *Voiding Dysfunction Following Cystourethropexy: Its Evaluation and Management*, J. Urol., 144 (1990).

With respect to sling procedures, if the sling mesh is too loosely associated with its intended physiological environment, the mesh may be ineffective in supporting the urethra and treating incontinence. Several complications can arise from a mesh that is too tightly placed including retention, sling erosion and other damage to surrounding tissue such as the urethra and vagina.

The TVT Tension-free Vaginal Tape procedure utilizes a knitted Prolene™ nonabsorbable, polypropylene mesh. The mesh is a substantially flat, rectangular woven article. The mesh includes a plurality of holes that are sized to allow tissue ingrowth to help avoid infection. A removable plastic sheath surrounds the mesh and is used during insertion of the mesh. The sling is positioned near the urethra without the use of bone anchors. Once the sheath is removed from the mesh of the TVT product, friction between the mesh and tissue keeps the mesh in position and it becomes very difficult to subsequently adjust the position of the mesh relative to tissue. Attempts to move the sling once the sheath is removed may damage the sling or adjacent tissue such as the urethra or vagina. In addition to issues with initial placement of the sling, other tensioning related issues are experienced by users of the TVT product post operatively.

Proper tension of a sling during and after the surgical intervention are important factors for successful treatment of incontinence. Surgical approaches to applying tension or slack in a sling procedure vary widely. See Decter, *Use of the Fascial Sling for Neurogenic Incontinence: Lessons Learned*, The Journal of Urology, Vol. 150, 683–686 (1993).

Other prior art sling procedures use bone anchors or other methods of securing a sling. A difficulty that contributes to the unnatural positioning of the urethra is that some attachment sites, such as the rectus abdominus fascia or the top of the pubic bone, require very long sutures. Long sutures increase the difficulty in achieving the proper tension in the sutures and sling and increase the chances that intervening anatomical structures may interfere with proper tension. Improper sling tension or sling suture tension can result in increased lateral movement and momentum of the support structures or mesh sling when they are moved due to intra-abdominal pressures.

Because many slings are anchored at anatomical positions remote from the urethra, proper tension in a sling is a difficult objective to achieve. Results can vary widely.

U.S. Pat. No. 5,863,315 discloses a method of tensioning a suspended tissue mass. The method utilizes a suture tensioner comprising a handle, a main body and an annular recess.

More than a year prior to the filing date of the present application, Vesica Sling Kits were sold (by Boston Scientific, Microvasive, USA) in the United States that included a Suture Spacer. Surgeons were instructed to place the Suture Spacer on the top of the pubic tubercle (which is a location remote from the sling and remote from the urethra, vagina and bladder neck). The surgeon then places a suture about the Suture Spacer and ties a knot. As a knot is tied, the Suture Spacer is pulled downward onto the top of the pubic bone. Six or seven additional throws are tied and the Suture Spacer is withdrawn.

U.S. Pat. No. 5,474,518 discloses a device for correcting urinary incontinence by use of vesical suspension. The device includes a box that houses a drum with a toothed wheel that engages a worm gear.

U.S. Pat. Nos. 4,938,760 and 4,969,892 disclose a method of suspending the urethrovesical junction in females. An anchoring means for anchoring a suture in tissue is disclosed. The anchoring means comprises a rotating spool, a driving gear and an adjusting means.

PCT International Pub. No. WO 01/39670 discloses an implantable support sheet for providing suburethral stabilization for female patients. A clip is disclosed that inhibits folding of a central part of the sheet about its longitudinal axis.

U.S. Pat. No. 6,106,545 discloses a suture tensioning and fixation device for attachment of tendon to muscle or reattachment of ligaments to bone. The device includes a retaining element and suture thread engaging portions.

U.S. Pat. No. 6,117,067 discloses a device for the height-adjustable fixing and support of internal organs. The device includes a sling, threads, tube, small capsule and chamber. A needle is used to introduce or extract liquid.

PCT Inter. Pub. No. WO 00/74633 discloses tape for an incontinence procedure that incorporates a suture. The suture is used in combination with a one way suture retaining device as disclosed in U.S. Pat. No. 5,669,935.

U.S. Pat. No. 6,068,591 discloses an apparatus for treatment of female stress urinary incontinence with a support harness. The patent discloses an adjustable setting and Carter pin.

BRIEF SUMMARY

In one aspect, the present invention comprises an adjustable article that is particularly suitable for urological applications such as sling procedures. In preferred embodiments, the article can have features that afford adjustment of the tension of the article postoperatively or perioperatively, or both.

In one embodiment, the present invention comprises an elongate biocompatible material (e.g. synthetic or non-synthetic or combinations thereof) having first and second major surfaces, and first and second ends defining an overall longitudinal axial length therebetween, at least one fold (preferably two and more preferably four folds) about the longitudinal axis so as to reduce the overall axial length of the implantable article, and releasable holding means for retaining the fold in a folded position and, upon release, for affording unfolding of the fold to increase the overall axial length.

In another embodiment, at least one fold reduces the overall axial length more than at least one other fold. This implant optionally includes a feature for informing the surgeon of the identity of the particular fold that is being released. As a result, the surgeon may select to adjust the implant by a predetermined amount.

A number of different releasable holding means are contemplated such as a biocompatible releasable adhesive or a structured surface. Preferably, the releasable holding means includes a filament element. The filament may be sized to extend from the implantable article through a vaginal incision. Alternatively, the releasable holding means may be constructed to be palpable through vaginal tissue without requiring an incision through vaginal tissue.

In a preferred embodiment, the filament is associated with the biocompatible material by being threaded therethrough without additional structure for associating the filament with the biocompatible material. This embodiment avoids undesirable tissue interaction or reaction with structure for connecting the sling to the filament. The filament may be associated with the biocompatible material in a fashion that affords release by pulling on the filament. In a preferred embodiment, the filament is free of a permanent connection to the biocompatible sling.

The implantable article optionally includes identification means for distinguishing at least one filament element from another filament element. For example, the identification means may comprise constructing one filament of a different color than another filament.

In another embodiment, the width of a fold is less than the width of the biocompatible material. This embodiment is believed particularly suitable for use with a relatively thick biocompatible material. This embodiment helps avoid creating relatively thick structures capable of harboring microorganisms and potentially leading to infection or other adverse consequences. For example, the biocompatible material may comprise a plurality of discrete lengths of a flat polypropylene material with a plurality of holes, and the fold may be provided by a folded or S-shaped filament that connects discrete, unfolded portions of the polypropylene.

Other optional features are also disclosed. For example, the filament may include grasping means such as handles. The releasable holding means may include locating means capable of being detected through vaginal tissue, and selected elements (e.g. the filament, sling or fold) may include a radioopaque material as an aid in identifying its location.

In another aspect, the implantable article of the present invention comprises an elongate biocompatible material having first and second major surfaces, first and second ends defining an overall longitudinal axial length therebetween, a mid portion and first and second end portions. The article includes an adjustment filament element axially woven through the biocompatible material so as to alternatively project above one major surface and then another major surface along the first end portion. The adjustment filament is associated with the biocompatiable material to afford a reduction or an increase in the overall length of the implantable article. The implantable article is constructed and arranged such that the mid portion of the biocompatible material may be placed adjacent target anatomical tissue such as the urethra without any filament element situated between a major surface of the mid portion of the biocompatible material and the target anatomical tissue. In this embodiment, the sling material is free of structure that projects above a major surface of the sling adjacent the urethra. As a result, this embodiment avoids structure that could adversely interact or damage sensitive tissue such as the urethra.

This embodiment preferably includes a second adjustment filament element axially woven through the biocompatible material so as to alternatively project above one major surface and then another major surface along the second end portion. The second adjustment filament is associated with the biocompatiable material to afford a reduction or an increase in the overall length of the implantable article. The adjustment filament may be sized to extend from the biocompatible material through a vaginal incision. Alternatively, an end portion of the adjustment filament may be constructed to be palpable through vaginal tissue without requiring the end portion to extend through a vaginal incision. Other features such as grasping and locating means may also be included in this embodiment.

In another aspect, the implantable article of the present invention comprises a method of treating incontinence comprising the steps of (i) providing a sling comprising an elongate biocompatible material having first and second major surfaces, edges, and first and second ends defining an overall longitudinal axial length therebetween, at least one fold about the longitudinal axis so as to reduce the overall axial length of the sling, and releasable holding means for retaining the at least one fold in a folded position and, upon release, for affording unfolding of the at least one fold to increase the overall axial length, (ii) implanting the sling, and (iii) releasing the releasable holding means to reduce the tension of the sling. In one embodiment, the method includes the steps of creating a vaginal incision, providing a filament element as the releasable holding means, extending the filament element through the vaginal incision, and the step of releasing the releasable holding means to reduce the tension of the sling includes the step of pulling on the portion of the filament element that extends through the vaginal incision.

In another aspect, the present invention comprises a method of treating incontinence including the steps of: (i) providing a sling comprising an elongate biocompatible material having first and second major surfaces, first and second ends defining an overall longitudinal axial length therebetween, a mid portion and first and second end portions, (ii) weaving an adjustment filament through the biocompatible material along at least a portion of the longitudinal axial so as to alternatively project above one major surface and then another major surface along the first end portion such that the length of the biocompatible material may be adjusted, (iii) implanting the sling such that the mid portion of the biocompatible material is situated adjacent the urethra without any filament element situated between a major surface of the mid portion of the biocompatible material and the urethra, and (iv) changing the tension of the sling by manipulating the filament.

Preferably, the step of changing the tension of the sling by manipulating the filament includes the step of tying a knot in the filament element just adjacent the mid portion of the biocompatible material. For example, the step of tying a knot may includes the step of tying an adjustable knot or a non-adjustable knot or combinations thereof.

BRIEF DESCRIPTION OF THE DRAWINGS

Other features and advantages of the present invention will be seen as the following description of particular embodiments progresses in conjunction with the drawings, in which:

FIG. 8 is a schematic perspective view showing a filament associated with a sling according to an embodiment of the present invention;

DETAILED DESCRIPTION

Disclosed herein is a detailed description of various illustrated embodiments of the invention. This description is not to be taken in a limiting sense, but is made merely for the purpose of illustrating the general principles of the invention. The section titles and overall organization of the present detailed description are for the purpose of convenience only and are not intended to limit the present invention.

Figure 1:
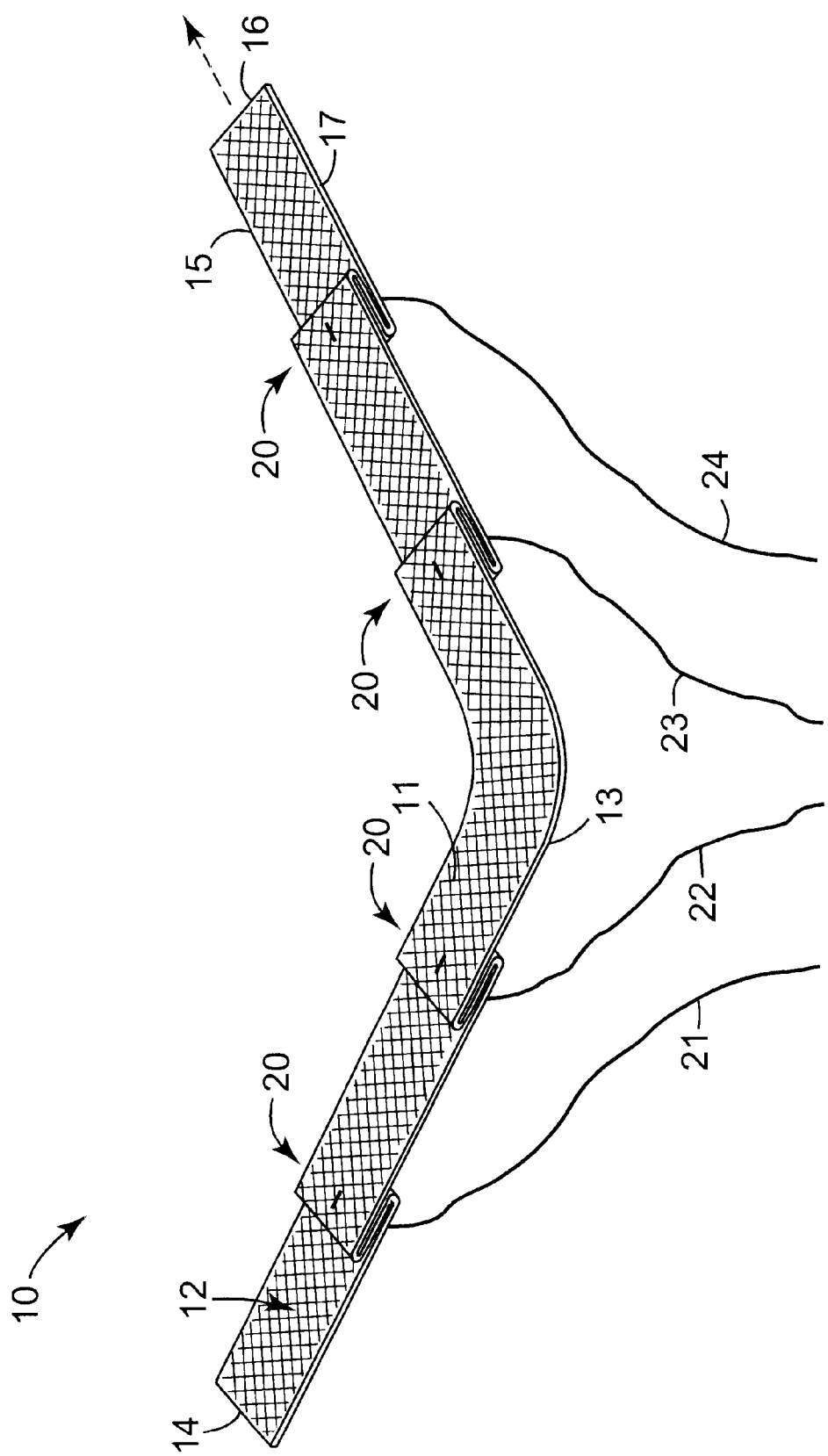
FIG. 1 is a perspective view of an embodiment of implantable article according to the present invention, showing portions of the sling in a folded position.
Figure 2:
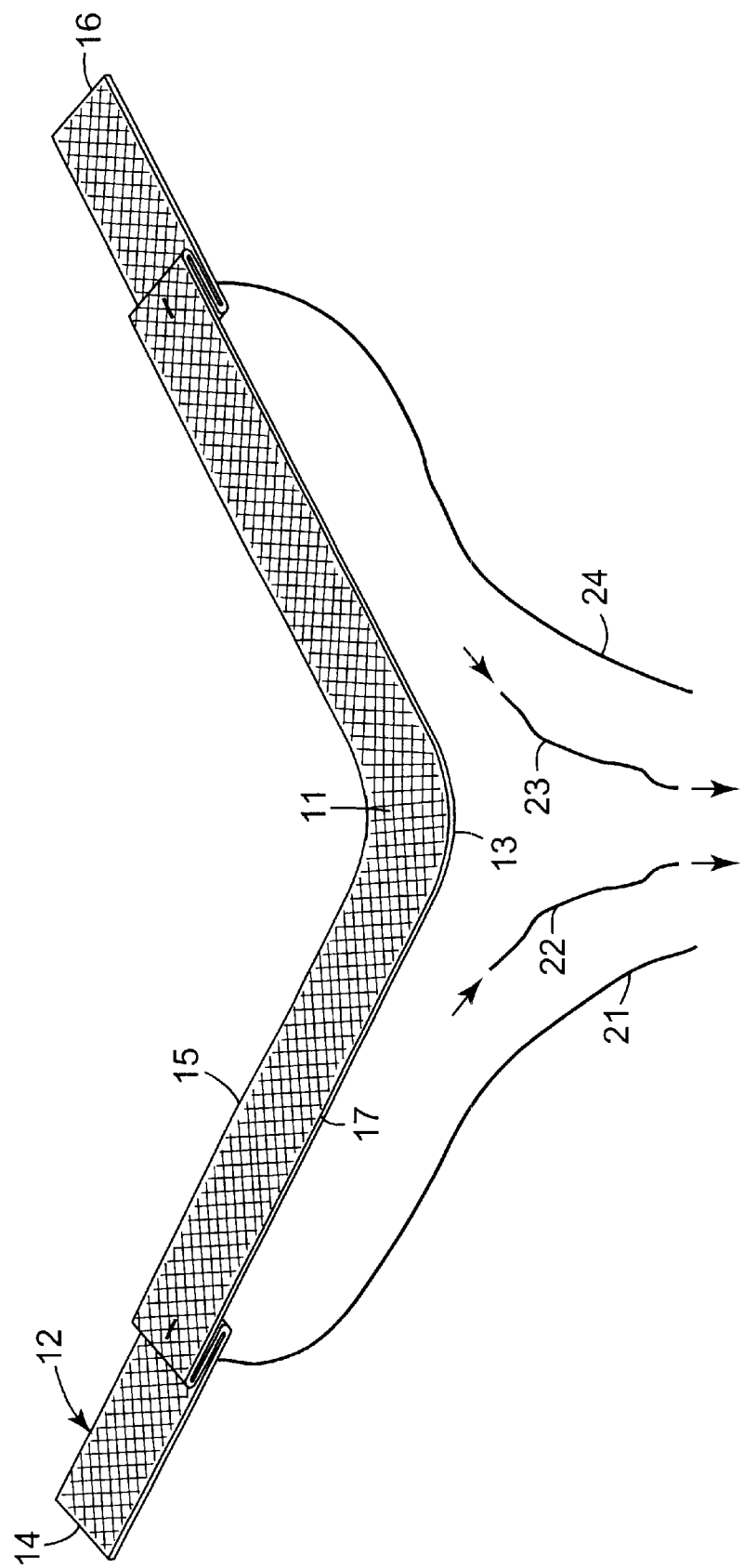
FIG. 2 is a perspective view of the implantable article of FIG. 1 showing portions of the implantable article in an unfolded position.

Referring to FIGS. 1 and 2, in one aspect, the present invention comprises an implantable article 10 for urological applications such as a sling procedure. The article 10 comprises an elongate biocompatible material 12 with first and second major surfaces 11, 13, edges 15, 17 and first and second ends 14, 16 defining an overall longitudinal axial length therebetween.

The article 10 includes at least one fold 20 about the longitudinal axis so as to reduce the overall axial length of the article 10. In the embodiment shown in FIG. 1, four folds 20 are shown.

The article also includes releasable holding means for retaining a fold in a folded position (see the middle two folds shown in FIG. 1) and, upon release, for affording unfolding of the fold to increase the overall axial length (see the middle two folds shown in an unfolded condition in FIG. 2) of the article 10. In a preferred embodiment, the releasable holding means comprises a filament element. In the embodiment shown in FIG. 1, four filamentary elements 21, 22, 23 and 24 are associated with the four folds 20.

The filament elements 21, 22, 23 and 24 are associated with the biocompatible material of the sling in a releasable fashion. Preferably, filament elements 21, 22, 23 and 24 afford release of a fold 20 by pulling on a leading end thereof.

The present invention contemplates a variety of approaches for associating the filament with the fold 20. For example, the filament may be tied to a portion of the fold. At least one knot may be used. The knot used to tie the filament to the biocompatible material 12 can be adjustable or non-adjustable (e.g. a surgeon's or friction knot). In a preferred embodiment, the knot may be releasable when a filament is pulled in one direction, and non-releasable when pulled in the other direction. Suitable knots for use in this and other embodiments of the present invention are described in the ETHICON Knot Tying Manual (© 1999–2000), available from ETHICON, of NJ. Alternatively, the filaments may be ultrasonically welded or adhesively adhered to the biocompatible material.

FIG. 8 illustrates another alternative for associating a filament 105 with a fold 20A in biocompatible material 12A. In this embodiment, the filament 105 is woven or threaded through the biocompatible material to provide a frictional association between the filament 105 and fold 20A without knotting the filament 105. To release the fold 20A, either leading end 101 or 103 of the filament may be pulled to remove the filament 105 from the fold 20A.

Figure 11:
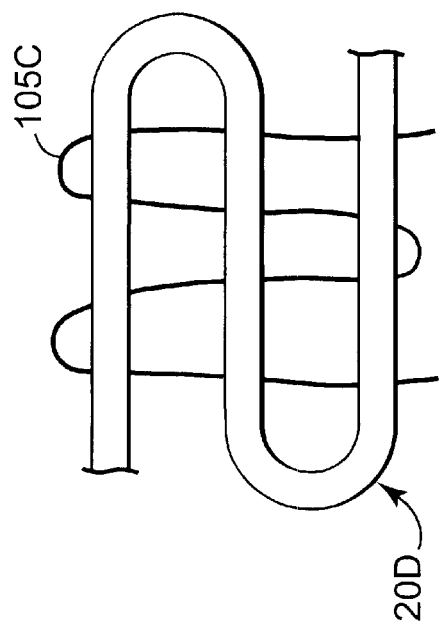
FIG. 11 is a schematic view of another embodiment of the association between a sling and filament according to a preferred embodiment of the present invention.
Figure 9:
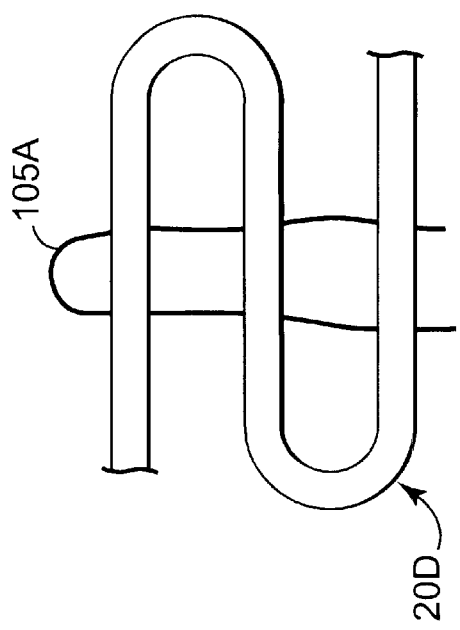
FIG. 9 is a schematic view of another embodiment of the association between a sling and filament according to a preferred embodiment of the present invention.
Figure 10:
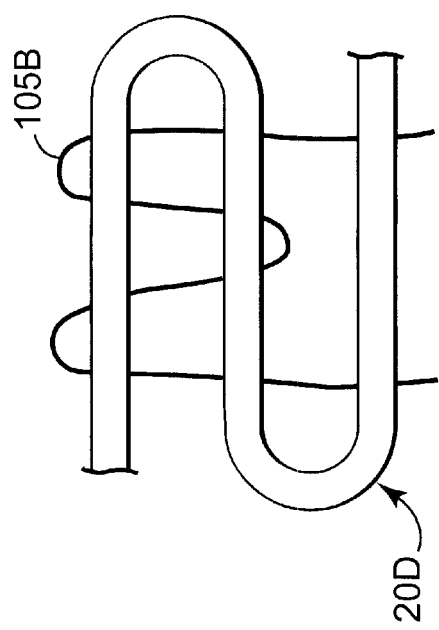
FIG. 10 is a schematic view of another embodiment of the association between a sling and filament according to a preferred embodiment of the present invention.

FIGS. 9, 10 and 11 show additional embodiments for associating a filament with a fold. In FIG. 9, filament 105A includes one direction change adjacent a major surface of the article, at the top of fold 20D. FIG. 10 illustrates a filament 105B with three direction changes, with one direction change situated below a middle portion of fold 20D. FIG. 11 illustrates a filament 105C with three direction changes, with one direction change situated below the bottom of the fold 20D.

Preferably, the association between a filament and fold affords release of the fold by pulling on the filament without requiring excessive or unreasonable force. The association should be sufficiently robust to resist premature release of a fold at least until tissue interaction with the implantable article (e.g. tissue ingrowth) reduces the opportunity for unwanted unfolding of the fold.

Alternatively, the filament may be permanently connected to (e.g. with a surgeon's knot, adhesive or weld) the sling and cut with a scissors to release the fold.

FIG. 1 shows two middle folds 20 shown in a folded position. To reduce tension in the article 10, filament elements 22 and 23 may be pulled and removed (as shown by the arrows in FIG. 2) to afford movement of the two middle folds toward an unfolded position as shown in FIG. 2. As a result, the axial length between ends 14 and 16 is longer in FIG. 2 than in FIG. 1. The increased axial length provided by unfolding the middle two folds can relieve tension in an implanted article such as a sling, and thereby reposition the sling to a therapeutically effective anatomical position or length.

In a preferred embodiment, the article 10 is a sling that is sized and shaped for treating urinary incontinence. Implantable article 10 may be used in conjunction with a wide variety of slings and procedures. For example, the present invention may be utilized in conjunction with the slings and procedures described in U.S. Pat. Nos. 5,520,700; 5,611,515; 5,842,478; 5,860,425; 5,972,000; 6,039,686, 6,042,534 and 6,110,101 (the entire contents of which are herein incorporated by reference in their entirety). Commercial examples of sling procedures that may be modified to incorporate the present invention include the In-Fast Sling System available from American Medical Systems of Minnetonka, Minn., and the trans vaginal TV Sling System available from Ethic on (a division of Johnson & Johnson).

The implantable article 10 is biocompatible. Suitable materials for the present invention include synthetic and non-synthetic materials. Suitable non-synthetic implantable materials include human fascia lata, treated animal (e.g. bovine or porcine or equine) tissue, autologous tissue, cadaver tissue, homografts, xenografts, heterografts, allografts and combinations of such materials. Suitable synthetic materials include knitted polypropylene slings alone, such slings with surrounding sheaths, or silicone coated polymer slings, such as those described in U.S. patent application Ser. No. 09/939,098 (entitled Coated Sling Material), filed Aug. 24, 2001. If a synthetic sling material is used, it preferably includes a plurality of holes that afford eventual tissue ingrowth.

Figure 3:
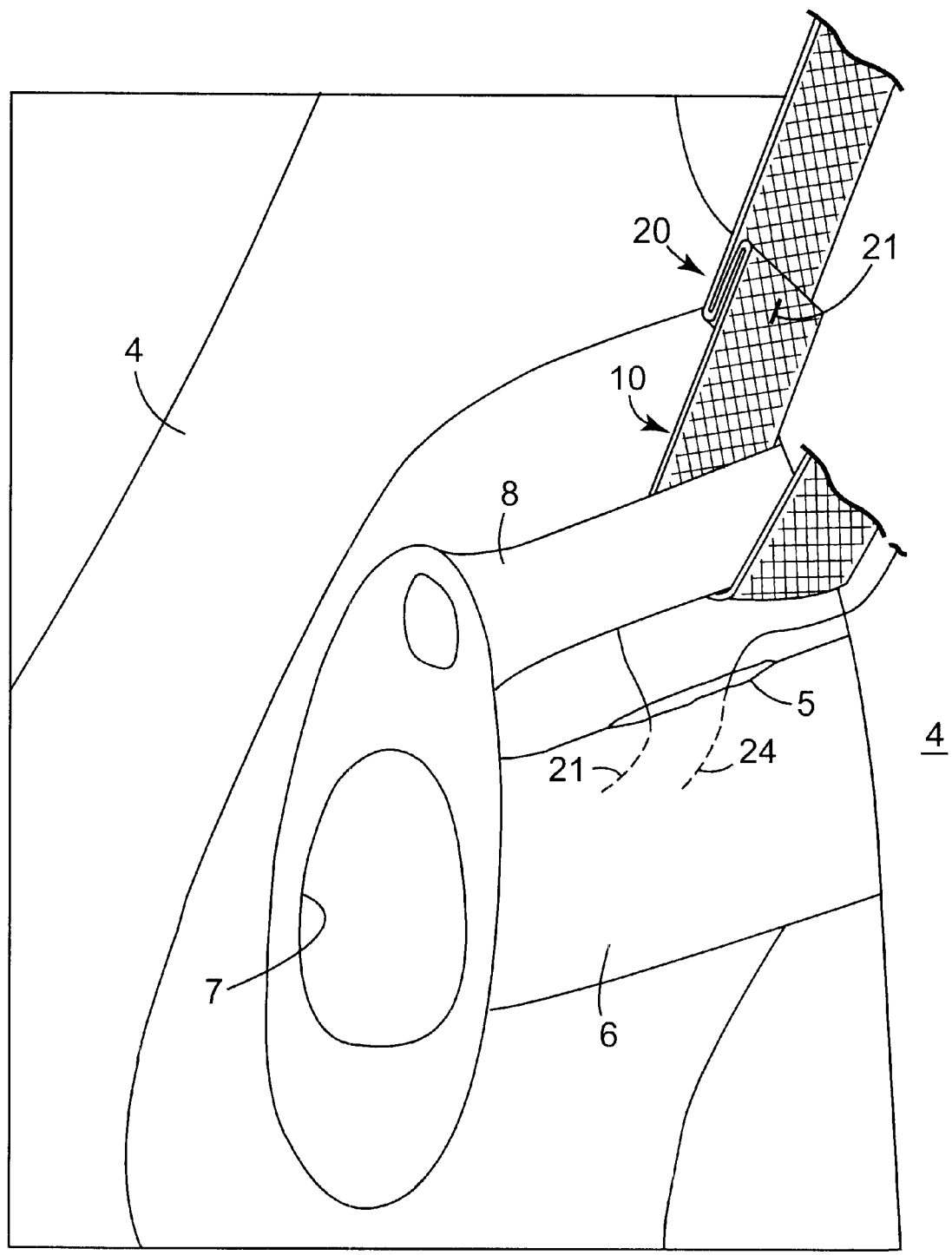
FIG. 3 is a schematic illustration of a sling implanted relative to a urethra and showing filament elements extending through a vaginal incision.

FIG. 3 illustrates article 10 implanted relative to the pubic bone 4, urethra 8 and vagina 6 of a patient. The middle two folds of the article (e.g. sling) 10 have been unfolded. In one embodiment, at least one of the filament elements (e.g. 21, 24) is sized to extend from the implantable article 10 through a vaginal incision 5. In this embodiment, filament elements 21 and 24 may be accessed through the opening 7 of the vagina 6 without requiring access through a vaginal incision 5. This feature affords adjustment of the tension of the sling 10 peri- and post operatively (e.g. after the surgical procedure) without reopening the patient or creating a subsequent incision. For example, after the vaginal incision 5 is closed, the filament elements 21 and 24 may be left projecting through the incision 5. If it becomes evident that the sling was too tightly placed relative to the urethra 8 (e.g. the patient is in retention), one or more of these projecting filament elements 21 and 24 may be subsequently pulled on and the sling unfolded to release tension in the implanted sling 10 to restore the sling 10 to a therapeutically effective position.

The filament elements 21, 22, 23 and 24 are constructed from a biocompatible material. They may be monofilaments or multifilaments (e.g. braided). Suitable materials include, but are not limited to, polypropylene, Dacron™, polyester, Gortex™ and nylon. Commercial examples include Ethibond Excel™ polyester fiber suture, the Ethilon™ nylon suture, the Mersilene™ polyester fiber suture, the Nurolon nylon suture and the Prolene polypropylene suture, each available from Ethicon.

The material of the filaments may be bioresorbable or non-bioresorbable (e.g. substantially permanent). As used herein, absorbable filament means a sterile strand prepared from a substance (e.g. collagen) derived healthy mammals or a synthetic polymer. Bioresorbable filaments may be constructed from materials of biological origin (e.g. surgical gut) and designed to be digested by tissue enzymes. Alternatively, a bioabsorbable filament may be constructed from a synthetic polymer designed to be broken down by hydrolysis. The absorbable filament may be treated or constructed to modify its resistance to absorption. It may also include an antimicrobial agent.

As used herein, a nonabsorbable filament means a strand of material that is suitably resistant to the action of living human tissue.

The cross section of the filament may be any suitable shape such as a circle, ellipse, square, rectangular or other polygonal shape.

A filament is preferably shaped like a line. However, other shaped filaments are also within the scope of the present invention including Y-shaped, X-shaped and Z shaped filaments.

In one embodiment, the present invention includes a synthetic sling with a plurality of holes. Once substantial tissue ingrowth occurs with a synthetic sling with a plurality of holes, the problems associated with permanently repositioning the sling relative to anatomical tissue increase. In a preferred embodiment, the material of the filament members (e.g. 21, 24) may be constructed of a material that remains operational (e.g. able to release fold 20) for a time period at least as long as a typical time period associated with tissue ingrowth into the holes of the synthetic sling. In the case of an absorbable filament, it may be designed to resist absorption until sufficient tissue interaction occurs to render the chances of undesirable lengthening of the sling remote.

Figure 7:
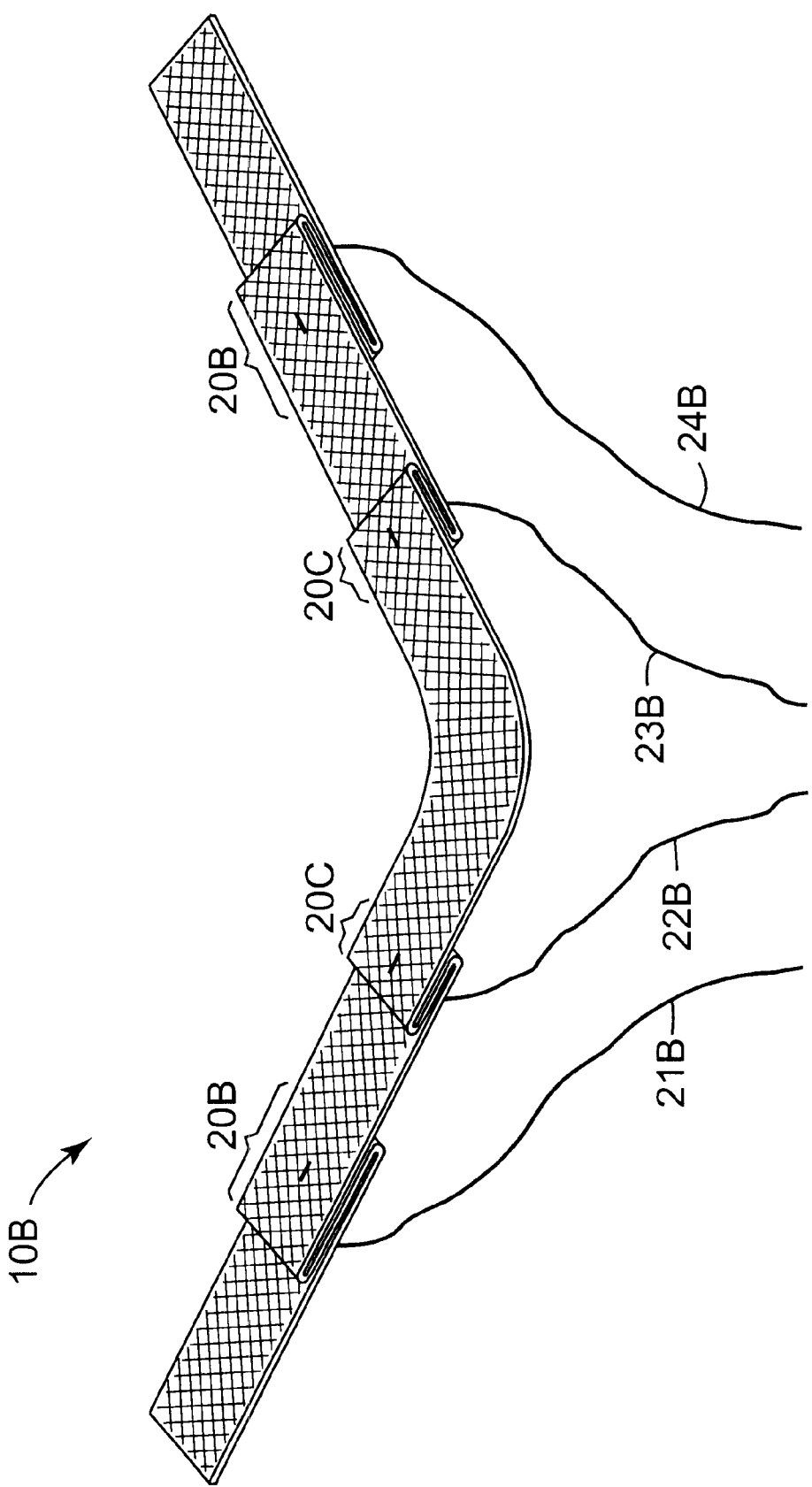
FIG. 7 is a perspective view of another embodiment of sling according to the present invention.

FIG. 7 illustrates another embodiment of the present invention. In this embodiment, the article 10B includes folds 20B and 20C of different sizes. Fold 20B reduces the overall length of implantable article 10B more than fold 20C. Optionally, filamentary elements 21B and 22B may include identification means for distinguishing filament element 21B (and its associated fold 20B) from another filament element 22B (and its associated fold 20C). As an example, the identification means may comprise constructing at least one filament element to be a color that is different than the color of the other filament element. This feature allows the surgeon to conveniently distinguish between sutures and associated folds and thus add more (by releasing filament 21B) or less (by releasing filament 22B) length according to the particular surgical need.

The identification means includes approaches other than color. For example, the identification means may include detectable substances (e.g. metals) or printed indicia.

Figure 4:
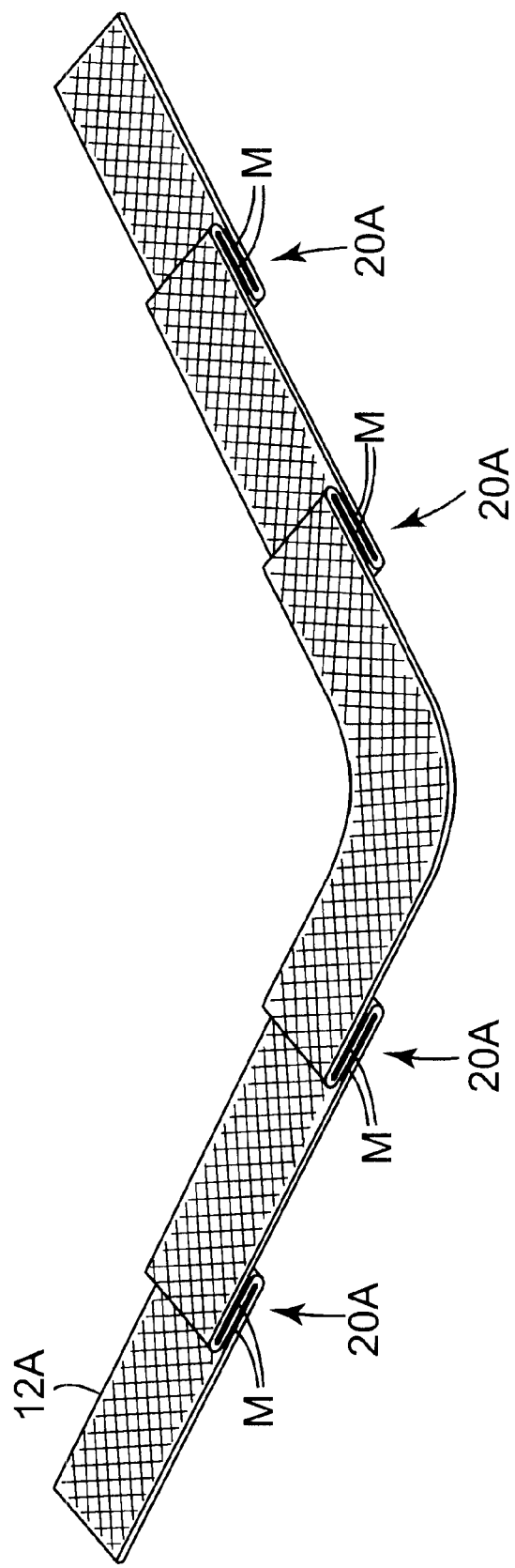
FIG. 4 is a perspective view of another embodiment of implantable article according to the present invention.

The releasable holding means associated with the present invention may comprise a feature other than a filament. FIG. 4 illustrates another embodiment of implantable article 12A according to the present invention. The implantable article 12A includes structured surfaces M on at least a portion of the major surfaces of article 12A within folds 20A.

Different types of structured surfaces are contemplated. The structured surface M may have a plurality of blunt tapered elements as taught in U.S. Pat. No. 4,875,259 to Appeldorn or U.S. Pat. No. 5,201,101 to Rouser et al. (the entire contents of each of which are herein expressly incorporated by reference). Alternatively, the structured surface M may be complementary structures such as hook and loop type fasteners. Many different hook and loop type fasteners are believed suitable for use in the present invention, such as the fasteners described in U.S. Pat. No. 3,359,980 to Rosenblatt, U.S. Pat. No. 3,694,867 to Stumpf, U.S. Pat. No. 3,913,183 to Brumlik, U.S. Pat. No. 4,609,581 to Ott, U.S. Pat. No. 4,739,635 to Conley et al., U.S. Pat. No. 4,761,318 to Ott et al. and U.S. Pat. No. 4,770,917 to Tochacek et al., the entire contents of each of which are herein expressly incorporated by reference. It is also believed that the fasteners described in U.S. Pat. No. 3,192,589 to Pearson, U.S. Pat. No. 3,353,663 to Kayser et al., U.S. Pat. No. 3,408,705 to Kayser et al., U.S. Pat. No. 4,959,265 to Wood et al., U.S. Pat. No. 5,077,870 to Melbye et al., and U.S. Pat. No. 5,196,266 to Lu et al., and EPO published application No. 382 420 to Lu et al. may also be used in accordance with the present invention. The particular structured surface chosen should be sufficiently blunt to avoid damaging surrounding tissue. It should also be sized and shaped to resist harboring microorganisms.

Alternatively, the releasable holding means shown in FIG. 4 may comprise a biocompatible, releasable adhesive. For example, the adhesive may comprise a pressure sensitive adhesive made in accordance with the teachings of U.S. Pat. No. 3,691,140 to Silver or a composition as disclosed in U.S. Pat. No. 5,385,606 to Kowanko. The adhesive may be pattern coated or flood coated on the applicable portion of the sling 12A. Commercial examples of compositions of suitable tissue adhesives include Tisseel fibrin sealant available from Baxter Healthcare Corp., of Glendale, Calif. or Beriplast fibrin sealant available from Centeon of King of Prussia, Pa.

The releasable holding means associated with the embodiments of the present invention described in conjunction with FIG. 4 are preferably release upon application of a substantially axial force to the implantable article 12A to achieve the desired release characteristic. The axial force may be applied during the surgical procedure (e.g. after a plastic sheath has been removed from the implantable article 12A) or after the initial vaginal incision is closed (post-operatively).

Figure 5:
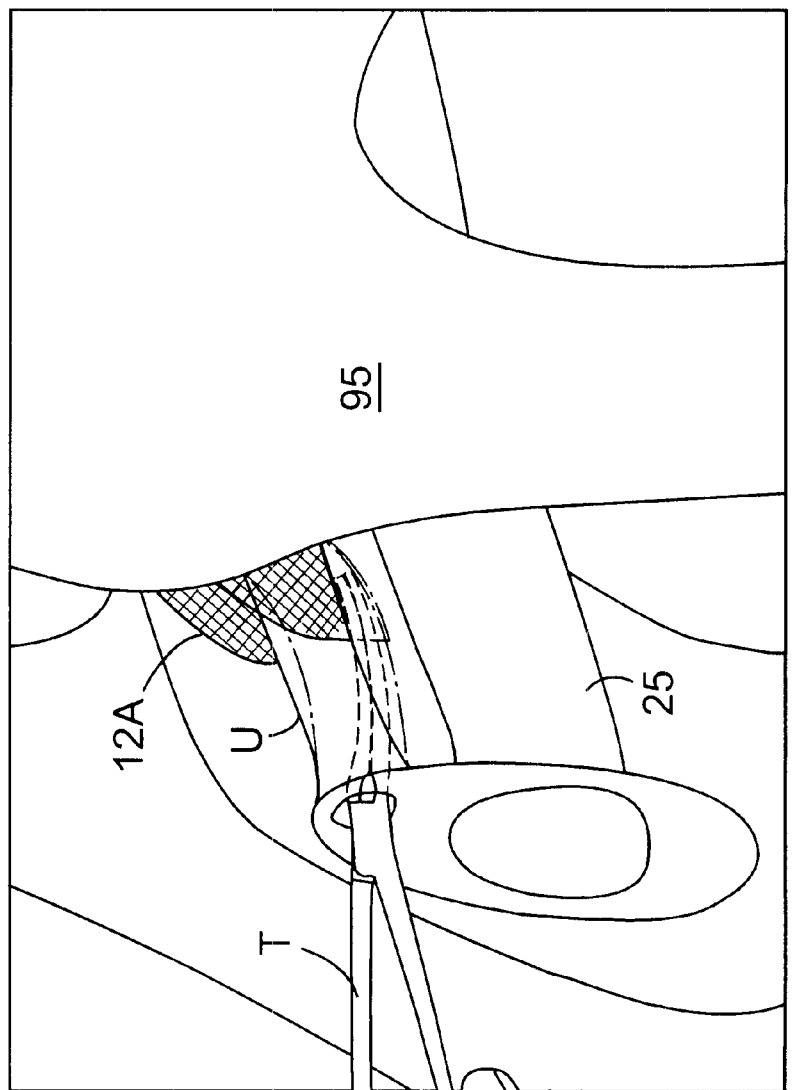
FIG. 5 is a schematic illustration of an example of a method for reducing the tension of the implantable article of FIG. 4 without reopening a vaginal incision.

FIG. 5 illustrates application of force to an implantable article 12A after a surgical procedure (e.g. after the original vaginal incision is closed). This figure illustrates the implantable article 12A (e.g. a sling) relative to the urethra U, vagina 25 and pubic bone 95 of the patient. In this example, a blunt instrument T is inserted into the urethra U post-operatively and pulled downward to apply an axial force to the sling 12A. The force releases one or more folds 20 and axially lengthens the sling 12A to reduce the tension applied by the sling 12A on the urethra U to reposition the sling 12A in a therapeutically effective position.

In an alternative embodiment, a slip knot may associate a filament with a fold. The slip knot may be designed to provide a substantially constant resistance to opening a fold. When an axial force is applied (e.g. as shown in FIG. 5), the slip knot is preferably constructed to afford gradual separation or unfolding of the fold. Once the axial force is lowered beyond a threshold provided by the slip knot (or stopped), the sling remains in the enlarged, partially unfolded condition.

Placing a blunt instrument T in the urethra U and moving it downward may also be used in conjunction with implantable article 10 after a filament element 21, 22, 23 or 24 is removed to assist in moving the implant 10 from a folded position (FIG. 1) to an unfolded position (FIG. 2).

In another embodiment of the present invention, the sling 12A may be designed such that the amount of axial force required to release one releasable holding means M is substantially different than the force required to release another releasable holding means on the sling 12A.

Figure 6:
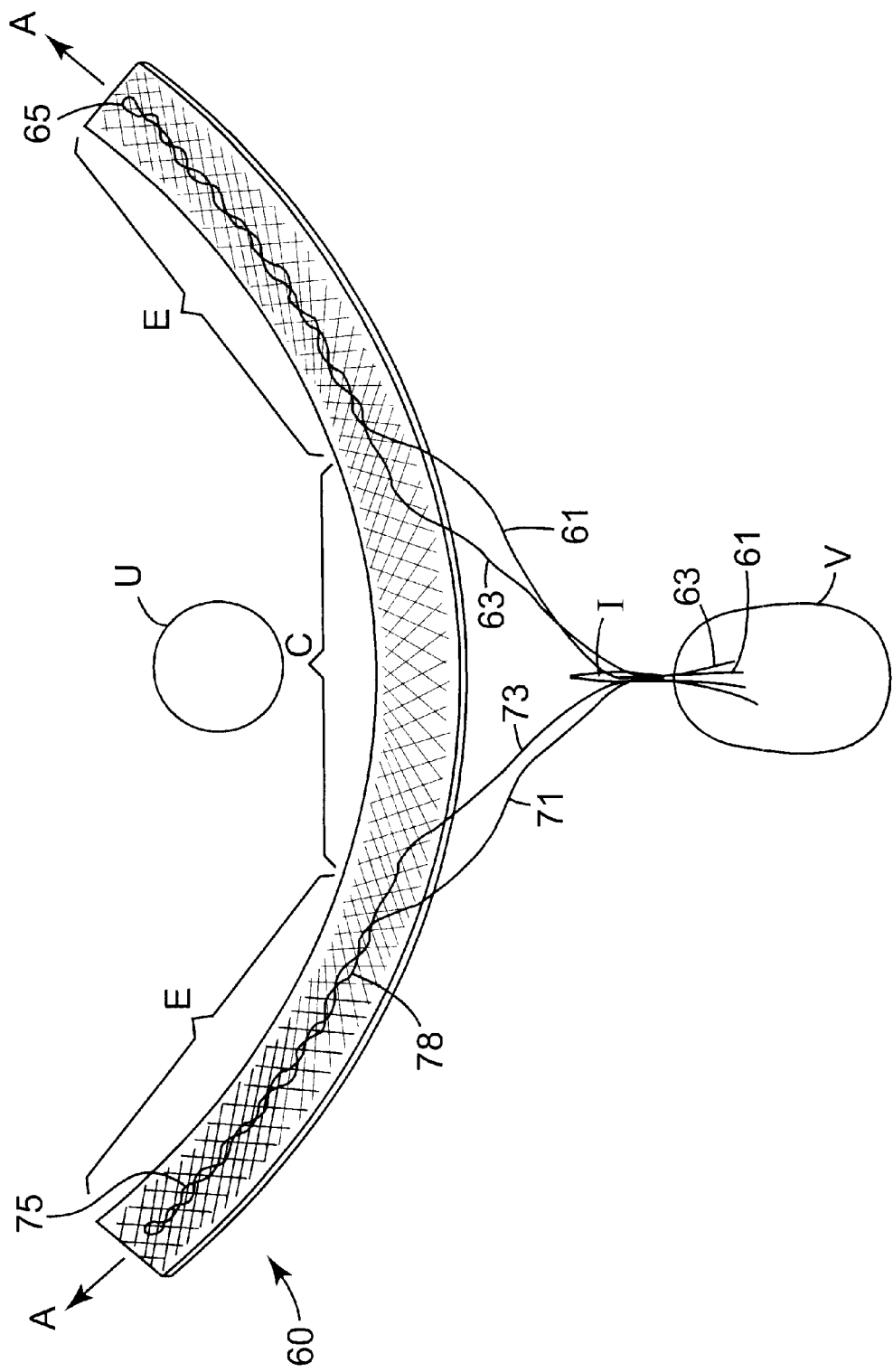
FIG. 6 is a perspective view of another embodiment of sling according to the present invention.

FIG. 6 illustrates another embodiment of the present invention. The article 60 comprises an elongate biocompatible material having first and second major surfaces, a pair of edges, first and second ends defining an overall longitudinal axial length therebetween (along axis A), a mid portion C and first and second end portions E.

Figure 15:
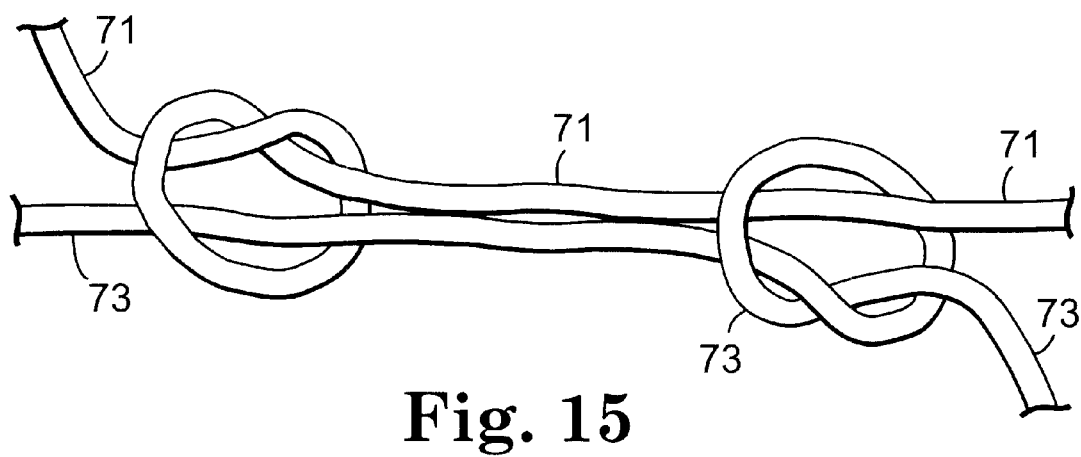
FIG. 15 is a side view of knots used to tie two filament ends together according to an embodiment of the present invention.

The article 60 has an adjustment filament element having a pair of end portions 71 and 73. The adjustment filament element is axially woven through the biocompatible material so as to alternatively project above (see reference character 75) one major surface and then another major surface (see reference character 78) a plurality of times along the first end portion E. The adjustment filament is associated with the biocompatible material to afford either a reduction or an increase of the tension of the implantable article 60. For example, to tighten the article 60, an axial tension force is applied to the end portions 71 and 73 of the filament resulting in a reduction of the overall length of the implantable article 60. Scores (e.g. transverse to the longitudinal axis A) or other weakening features may be applied along the end portion E to help control or facilitate the shortening of the end portion E. The ends 71 and 73 may then be tied in a surgeon's knot or, alternatively, the knot shown in FIG. 15.

Implantable article 60 is constructed and arranged such that the mid portion C of the biocompatible material may be placed adjacent target anatomical tissue such as the urethra U without any filament element situated between a major surface of the mid portion C of the biocompatible material and the urethra U.

The article 60 preferably has a second adjustable filament element 65 having a pair of end portions 61 and 63. Like the first filament element, the second filament element is axially woven through the biocompatible material so as to alternatively project above one major surface and then another major surface a plurality of times along the second end portion E such that an axial tension force applied to the end portions 61 and 63 of the second filament element affords a reduction of the overall length of the implantable article 60.

Figure 12:
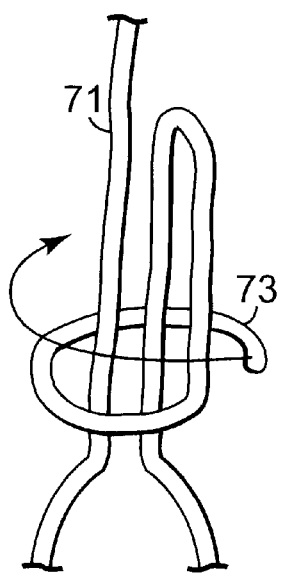
FIGS. 12, 13 and 14 are side views that sequentially illustrate steps in tying an adjustable knot according to an embodiment of the present invention.
Figure 13:
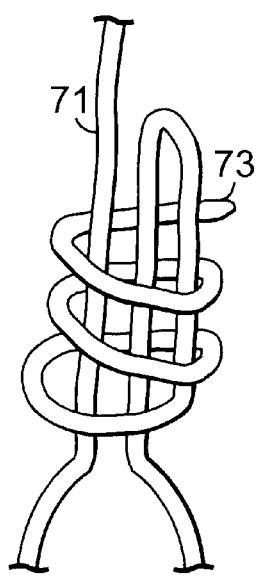
Figure 14:
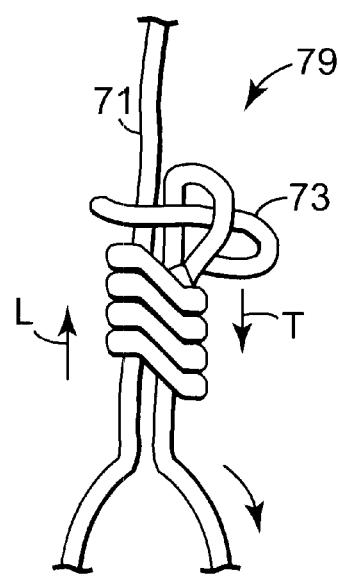

The first or second filaments 75 and 65 may also be used to lengthen the article 60 after it is implanted. For example, the ends 71 and 73 can be tied in the adjustable knot 79 shown in FIG. 14. FIGS. 12–14 sequentially illustrate how to tie adjustable knot 79 using ends 71 and 73. Alternative adjustable knots are also contemplated for use in the present invention. To provide an implantable article 60 that can be tightened or loosed, the adjustable knot 79 is initially adjusted to reduce the length of the article 60 from its maximum length. The implantable article 60 is then implanted in the patient with a length less than its maximum length. Should the implantable article 60 thereafter need to be tightened, the knot 79 is moved in the direction T shown in FIG. 14. This will cause the overall length of the sling to shorten. Should the implantable article thereafter need to be loosened, the knot 79 is moved in the direction L (opposite direction T) shown in FIG. 14. This will cause the length to be increased toward its maximum length.

In FIG. 6, the end portions 61, 63 or 71, 73 of the first or second filament element are sized to extend from the biocompatible material and project through a vaginal incision I into the vagina V. In a preferred embodiment, the end portions do not extend through the vaginal incision.

Figure 16:
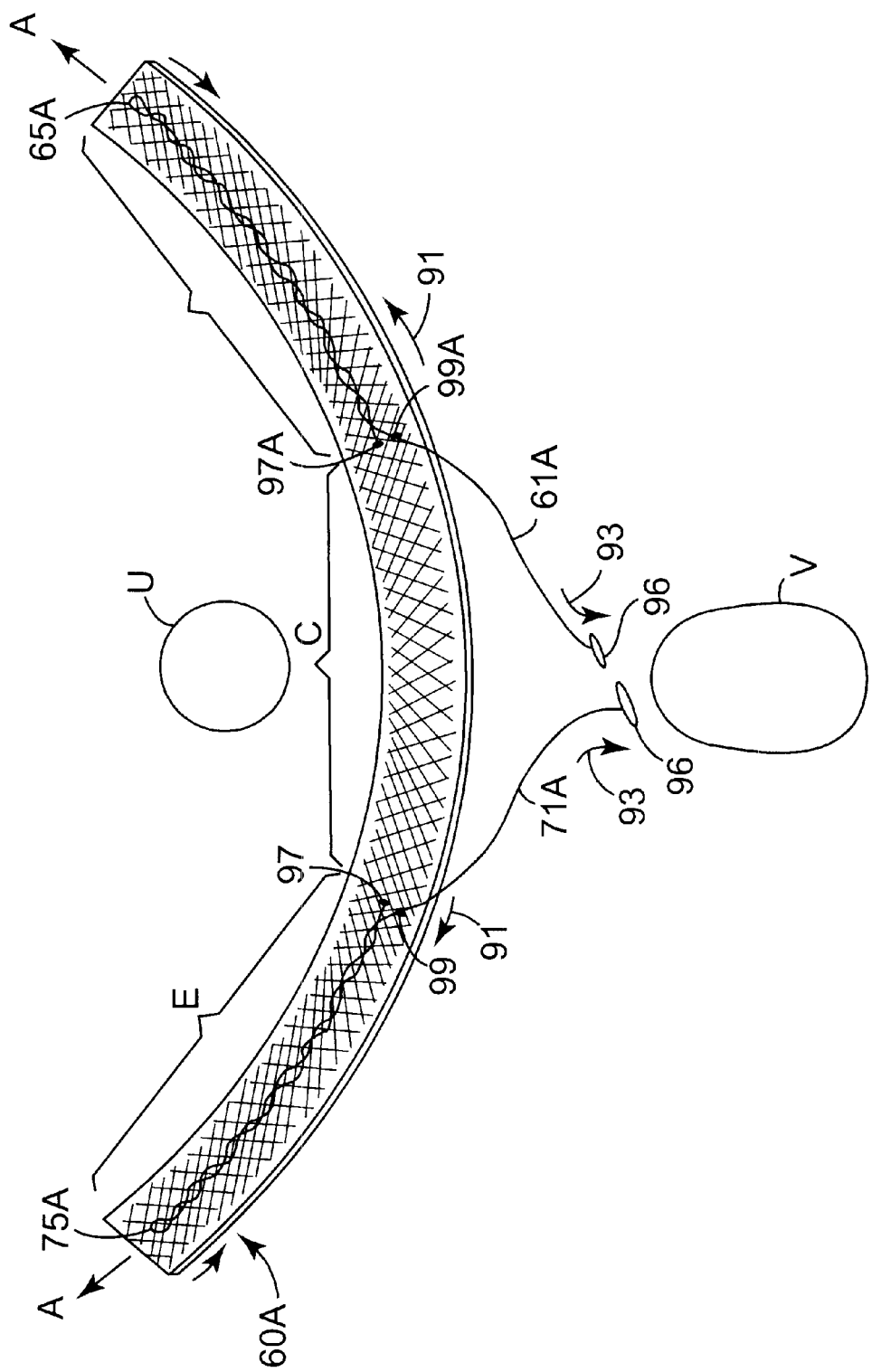
FIG. 16 is a perspective view of another embodiment of sling according to the present invention.

FIG. 16 illustrates an alternative sling 60A according to the present invention. The sling 60A includes filaments 65A and 75A. One end of filaments 75A is permanently tied (e.g. with a surgeon's knot) to the sling at location 97. One end of filaments 65A is permanently tied (e.g. with a surgeon's knot) to the sling at location 97A. Adjustable knots in filaments 65A and 75A are provided at locations 99 and 99A. When the ends 71A and 61A of filaments 65A and 75A are pulled in the direction shown by the arrows 93 in FIG. 16, the adjustable knot at location 99 affords a reduction in the length of the sling in the direction of arrows 91. The adjustable knot is tied to retain the sling in the reduced length condition.

A filament element 65A or 75A may be sized and shaped to be palpable through vaginal tissue V without requiring an incision through the vaginal tissue V. Optionally biocompatible handles 96 can be provided so that the surgeon can clamp onto and adjust filament elements 65A or 75A without requiring an incision through vaginal tissue. Also optionally, the filament or handles may include locating means capable of being detected through vaginal tissue. For example, the filament, adjustable knot or handle may be constructed from a radioopaque material to assist the surgeon in locating the adjustable features of the sling.

In another embodiment, the width of a fold may be substantially less than the width of the biocompatible material. The fold of the present invention may be constructed from a material different than the rest of the sling. These features are believed particularly suitable for use with a relatively thick sling material and help avoid providing relatively thick, implanted structures capable of harboring microorganisms and potentially leading to infection or other adverse consequences. For example, the biocompatible material of the sling may comprise at least two discrete lengths of a flat polypropylene material with a plurality of holes, and a fold may be provided by a folded or S-shaped filament that connects discrete, unfolded portions of the polypropylene sling material. Another filament may be used as a releasable holding means to releasably retain the folded filament in the folded condition.

Method

In another aspect, the present invention comprises a method of changing tension in an implantable article. Tension may be loosened or increased.

Loosening

In one aspect, the present invention comprises a method of treating incontinence. The method comprises the steps of (1) providing a sling (e.g. 10) comprising an elongate biocompatible material 12 having first and second major surfaces, edges, and first and second ends 14, 16 defining an overall longitudinal axial length therebetween, at least one fold 20 about the longitudinal axis so as to reduce the overall axial length of the sling, and releasable holding means (e.g. 21, 22, 23 and 24) for retaining the fold 20 in a folded position and, upon release, for affording unfolding of the fold 20 to increase the overall axial length of the sling 10, (2) implanting the sling 10 in a patient, and (3) releasing the releasable holding means to reduce the tension of the sling 10.

In a preferred embodiment, the method further includes the steps of: creating a vaginal incision 5 (see FIG. 3), providing a filament element (e.g. 21, 22, 23 or 24) as the releasable holding means, and extending the filament element through the vaginal incision (e.g. see FIG. 3). In this preferred embodiment, the step of releasing the releasable holding means includes the step of pulling on the portion of the filament element that extends through the vaginal incision 5 to separate the filament element from the implantable article 10. With nothing holding the fold at this point, it may be unfolded (see FIG. 2). Unfolding the fold reduces the tension of the sling by providing more axial length in the sling.

Alternatively, the filaments need not extend through the vaginal incision. Instead, they may be constructed to be palpable or detectable through the vaginal tissue (e.g. by use of handles, or radioopaque elements). As a result, they may be detected and manipulated before or after the surgical incision in the vagina is closed.

In another aspect, the present invention may comprise a method of treating incontinence comprising the steps of: (1) providing a sling (e.g. 12A of FIG. 4) comprising an elongate biocompatible material having first and second major surfaces, edges, and first and second ends defining an overall longitudinal axial length therebetween, at least one fold 20A about the longitudinal axis so as to reduce the overall axial length of the sling, and releasable holding means M for releasably retaining the fold 20A in a folded position and, upon release, for affording unfolding of the fold 20A to increase the overall axial length of the sling 12A, (2) implanting the sling 12A, and (3) releasing the releasable holding means to reduce the tension of the sling 12A.

In a preferred embodiment, the step of releasing the releasable holding means to reduce the tension of the implanted sling includes the step of applying a substantially axial force to the sling (e.g. see FIG. 5).

In yet another method, a sling is provided that is held in a length less than a maximum length of the sling by an adjustable knot (e.g. 79). The sling is implanted. The knot 79 is then moved in a loosening direction (e.g. L in FIG. 14) in order to reduce the tension of the sling. The knot 79 may be palpable or detectable through vaginal tissue. Grasping the knot 79, filament or sling through the vaginal tissue (e.g. with a surgical clamp) affords the opportunity to adjust the tension of the sling post operatively without the need for an addition incision.

Tightening

In another aspect, the present invention comprises a method of treating incontinence comprising the steps of: (1) providing a sling (e.g. 60) comprising an elongate biocompatible material having first and second major surfaces, first and second ends defining an overall longitudinal axial length therebetween (along axis A), a mid portion C and first and second end portions E, (2) axially weaving a first filament element through the biocompatible material so as to alternatively project above one major surface and then another major surface along the first end portion such that an axial tension force applied to the first filament element affords a reduction of the overall length of the sling, (3) implanting the sling such that the mid portion C of the biocompatible material is situated adjacent the urethra without any filament element situated between a major surface of the mid portion of the biocompatible material and the urethra, and (4) increasing the tension of the sling by pulling on the ends of the first filament element. The ends may thereafter be tied in an adjustable or non-adjustable knot to set the tension of the sling.

Preferably, the step of increasing the tension of the sling by pulling on the filament element includes the step of tying a knot in the filament element at an interface of the mid portion C of the biocompatible material and an end portion E (see FIG. 6).

In yet another method, a sling is provided with an adjustable knot (e.g. 79). The sling is implanted. The knot 79 is then moved in a tightening direction (e.g. T in FIG. 14) in order to increase the tension of the sling by reducing its overall length. The knot 79 may be palpable or detectable through vaginal tissue. Grasping the knot 79, filament or sling through the vaginal tissue (e.g. with a surgical clamp) affords the opportunity to adjust the tension of the sling post operatively without the need for a subsequent or additional incision.

It is understood that the embodiments of the invention disclosed herein are illustrative of the principles of the invention. Other modifications may be employed which are within the scope of the invention; thus, by way of example but not of limitation, alternate filament and fold shapes, alternate sling shapes, and use with alternative anatomical support materials. Accordingly, the present invention is not limited to that precisely as shown and described in the present application.

What is claimed is:

1. An implantable article for urological applications such as a sling procedure, the article comprising:
    an elongate biocompatible material having first and second major surfaces, edges and first and second ends defining an overall longitudinal axial length therebetween,
    at least one fold about the longitudinal axis so as to reduce the overall axial length, and
    releasable holding means for retaining the at least one fold in a folded position and, upon release, for affording unfolding of the at least one fold to reduce the tension of the implantable article,
    wherein the releasable holding means comprises a filament element, and
    wherein the filament element is sized to extend from the implantable article through a vaginal incision.

2. An implantable article according to claim 1 comprising at least two folds.

3. An implantable article according to claim 1 comprising at least two folds, and at least one fold reduces the overall axial length more than at least one other fold.

4. An article according to claim 3 wherein the releasable holding means comprise filament elements, and
    identification means for distinguishing at least one filament element from another filament element to afford a predetermined release of tension.

5. An article according to claim 9 wherein the identification means comprises constructing at least one filament element in a color that is different than a color of at least one other filament element.

6. An article according to claim 1 wherein the biocompatible material comprises a synthetic material.

7. An article according to claim 1 wherein the at least one fold extends substantially transverse to the longitudinal axis.

8. An article according to claim 1 wherein the filament is associated with the biocompatible material in a fashion that affords release by pulling on the filament element.

9. An article according to claim 1 wherein the filament is associated with the biocompatible material by being threaded therethrough without additional structure for associating the filament with the biocompatible material.

10. An article according to claim 1 wherein the filament element is constructed to be palpable through vaginal tissue so that it can be adjusted without requiring an incision through vaginal tissue.

11. An article according to claim 10 wherein the filament includes grasping means.

12. An article according to claim 1 wherein the filament includes locating means capable of being detected through vaginal tissue.

13. An article according to claim 12 wherein the locating means comprises a radioopaque handle.

14. An article for urological applications such as a sling procedure, the article comprising:
    an elongate biocompatible material having first and second major surfaces, edges and first and second ends defining an overall longitudinal axial length therebetween,
    at least one fold about the longitudinal axis so as to reduce the overall axial length, and
    releasable holding means for retaining the at least one fold in a folded position and, upon release, for affording unfolding of the at least one fold to reduce the tension of the implantable article, and
    wherein the biocompatible material comprises non-synthetic material.

15. An article according to claim 14 wherein the releasable holding means comprises a biocompatible releasable adhesive.

16. An article according to claim 14 wherein the releasable holding means comprises a structured surface.

17. An implantable article according to claim 14 wherein the biocompatible material has a width between its edges,
    the at least one fold has a width, and
    the width of the at least one fold is less than the width of the biocompatible material.

18. An article for urological applications such as a sling procedure, the article comprising:
    an elongate biocompatible material having first and second major surfaces, edges and first and second ends defining an overall longitudinal axial length therebetween,
    at least two folds about the longitudinal axis so as to reduce the overall axial length,
    releasable holding means for retaining the at least two folds in a folded position and, upon release, for affording unfolding of at least one fold to reduce the tension of the implantable article,
    wherein a releasable holding means is associated with each fold and each releasable holding means is adapted to release upon application of a substantially axial force applied to the biocompatible material, and
    wherein the amount of axial force required to release one releasable holding means is substantially different than the force required to release another releasable holding means.

19. An implantable article according to claim 1 wherein the releasable holding means is free of a permanent connection to the implantable article.

20. An implantable article for urological applications such as a sling procedure, the article comprising:
    an elongate biocompatible material having first and second major surfaces, edges and first and second ends defining an overall longitudinal axial length therebetween,
    at least one fold about the longitudinal axis so as to reduce the overall axial length, releasable holding means for retaining the at least one fold in a folded position and, upon release, for affording unfolding of the at least one fold to reduce the tension of the implantable article, wherein the biocompatible material comprises a polypropylene with a plurality of holes, and the at least one fold is provided by a folded filament connected to discrete, unfolded portions of the biocompatible material.

21. An implantable article for urological applications such as a sling procedure, the article comprising:

an elongate biocompatible material having first and second major surfaces, a pair of edges, first and second ends defining an overall longitudinal axial length therebetween, a mid portion and first and second end portions, an adjustment filament element axially woven through the biocompatible material so as to alternatively project above one major surface and then another major surface along the first end portion, the adjustment filament being associated with the biocompatiable material to afford a reduction or an increase in the tension of the implantable article, and wherein the article is constructed and arranged such that the mid portion of the biocompatible material may be placed adjacent to target anatomical tissue such as the urethra without any filament element situated between a major surface of the mid portion of the biocompatible material and the target anatomical tissue.

22. An article according to claim 21 further comprising a second adjustment filament element axially woven through the biocompatible material so as to alternatively project above one major surface and then another major surface along the second end portion, the second adjustment filament being associated with the biocompatiable material to afford a reduction or an increase in the tension of the implantable article.

23. An article according to claim 21 wherein end portions of the adjustment filament element are sized to extend from the biocompatible material through a vaginal incision.

24. An article according to claim 21 wherein an end portion of the adjustment filament is constructed to be palpable through vaginal tissue without requiring an incision through vaginal tissue.

25. An article according to claim 21 wherein the adjustment filament includes grasping means.

26. An article according to claim 21 wherein the adjustment filament includes locating means capable of being detected through vaginal tissue.

27. An article according to claim 26 wherein the locating means comprises a radioopaque element.

28. A method of treating incontinence comprising the steps of:

providing a sling comprising an elongate biocompatible material having first and second major surfaces, edges, and first and second ends defining an overall longitudinal axial length therebetween, at least one fold about the longitudinal axis so as to reduce the overall axial length of the sling, and releasable holding means for retaining the at least one fold in a folded position and, upon release, for affording unfolding of the at least one fold to increase the overall axial length, implanting the sling, releasing the releasable holding means to reduce the tension of the sling, creating a vaginal incision, providing a filament element as the releasable holding means, extending the filament element through the vaginal incision, and the step of releasing the releasable holding means to reduce the tension of the sling includes the step of pulling on the portion of the filament element that extends through the vaginal incision to separate the filament from the fold.

29. A method of treating incontinence comprising the steps of:

providing a sling comprising an elongate biocompatible material having first and second major surfaces, first and second ends defining an overall longitudinal axial length therebetween, a mid portion and first and second end portions, axially weaving a first filament element through the biocompatible material so as to alternatively project above one major surface and then another major surface along the first end portion such that the length of the biocompatible material may be adjusted, implanting the sling such that the mid portion of the biocompatible material is situated adjacent the urethra without any filament element situated between a major surface of the mid portion of the biocompatible material and the urethra; and manipulating the filament element to increase or decrease the tension of the sling.

30. A method according to claim 29 wherein the step of manipulating the filament element to increase or decrease the tension of the sling includes the step of tying a knot in the filament element just adjacent the mid portion of the biocompatible material.

31. A method according to claim 30 wherein the step of tying a knot includes the step of tying an adjustable knot.

* * * * *